United States Patent
McArthur et al.

(10) Patent No.: US 7,259,158 B2
(45) Date of Patent: Aug. 21, 2007

(54) NAPHTHALINE DERIVATIVES AS H3 INVERSE AGONISTS

(75) Inventors: Silvia Gatti McArthur, Basel (CH); Cornelia Hertel, Muenchenstein (CH); Matthias Heinrich Nettekoven, Grenzach-Wyhlen (DE); Jean-Marc Plancher, Hagenthal le bas (FR); Susanne Raab, Basel (CH); Olivier Roche, Folgensbourg (FR); Rosa Maria Rodriguez-Sarmiento, Basel (CH); Franz Schuler, Riehen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 150 days.

(21) Appl. No.: 11/142,738

(22) Filed: Jun. 1, 2005

(65) Prior Publication Data

US 2006/0009449 A1     Jan. 12, 2006

(30) Foreign Application Priority Data

Jun. 2, 2004    (EP)   ................................. 04102460

(51) Int. Cl.

| | |
|---|---|
| C07D 211/14 | (2006.01) |
| C07D 213/02 | (2006.01) |
| C07D 403/10 | (2006.01) |
| C07D 211/20 | (2006.01) |
| C07D 417/10 | (2006.01) |
| C07D 413/10 | (2006.01) |
| C07D 401/10 | (2006.01) |

(52) U.S. Cl. ............................. 514/212.01; 514/227.8; 514/237.8; 514/318; 514/326; 546/186; 546/193; 546/208; 546/236; 544/60; 544/129; 540/597

(58) Field of Classification Search ........... 514/212.01, 514/227.8, 237.8, 318, 326; 546/186, 193, 546/208, 236; 544/60, 129; 540/597

See application file for complete search history.

(56) References Cited

U.S. PATENT DOCUMENTS

2006/0084679 A1*   4/2006   McArthur et al. .......... 514/314

FOREIGN PATENT DOCUMENTS

| | | |
|---|---|---|
| WO | WO 02/076925 A2 | 10/2002 |
| WO | WO 2004/037788 A1 | 5/2004 |
| WO | WO 2004/043458 A1 | 5/2004 |

OTHER PUBLICATIONS

Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.

* cited by examiner

*Primary Examiner*—Kamal A. Saeed
*Assistant Examiner*—Nyeemah Grazier
(74) *Attorney, Agent, or Firm*—George W. Johnston; Dennis P. Tramaloni; Samuel H. Megerditchian

(57) ABSTRACT

The present invention relates to compounds of formula I:

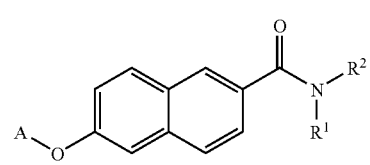

and pharmaceutically acceptable salts thereof, to the preparation of such compounds and pharmaceutical compositions containing them. The compounds are useful for the treatment and/or prevention of diseases which are associated with the modulation of H3 receptors.

12 Claims, No Drawings

NAPHTHALINE DERIVATIVES AS H3 INVERSE AGONISTS

FIELD OF THE INVENTION

The present invention relates to novel naphthaline derivatives of the formula I:

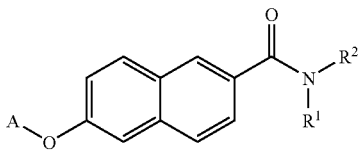

and pharmaceutically acceptable salts thereof, their manufacture, pharmaceutical compositions containing them and their use as medicaments. The compounds of formula I are antagonists and/or inverse agonists at the histamine 3 receptor (H3 receptor) and are useful in treating obesity and other disorders.

All documents cited or relied upon below are expressly incorporated herein by reference.

BACKGROUND OF THE INVENTION

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the central nervous system (CNS) and the periphery through four distinct histamine receptors, the histamine H1, H2, H3 and H4 receptors. H3 receptors are predominantly localized in the CNS. As an autoreceptor, H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release.

Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11). A need exists, therefore, to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

The invention relates to a compound of the formula I:

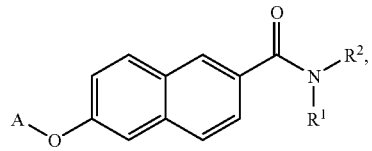

wherein:

$R^1$ is selected from the group consisting of hydrogen, lower alkyl, phenyl unsubstituted or substituted with one or two groups independently selected from the group consisting of lower alkyl, lower halogenalkoxy and lower hydroxyalkyl, lower phenylalkyl, wherein the phenyl ring is unsubstituted or substituted with one or two groups independently selected from the group consisting of lower alkyl, halogen, lower alkoxy and lower hydroxyalkyl, and lower alkoxyalkyl;

$R^2$ is selected from the group consisting of hydrogen, lower alkyl, cycloalkyl, lower cycloalkylalkyl, lower hydroxyalkyl, lower alkoxyalkyl, lower alkylsulfanylalkyl, lower dialkylaminoalkyl, phenyl unsubstituted or substituted with one or two groups independently selected from the group consisting of lower alkyl, halogen, lower alkoxy and lower hydroxyalkyl, lower phenylalkyl, wherein the phenyl ring is unsubstituted or substituted with one or two groups independently selected from the group consisting of lower alkyl, halogen, lower alkoxy and lower hydroxyalkyl, pyrrolidinyl unsubstituted or substituted with a group selected lower alkyl or halogen, lower heteroarylalkyl, wherein the heteroaryl ring is unsubstituted or substituted with one or two lower alkyl groups, and lower heterocyclylalkyl, wherein the heterocyclyl ring is unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen;

A is

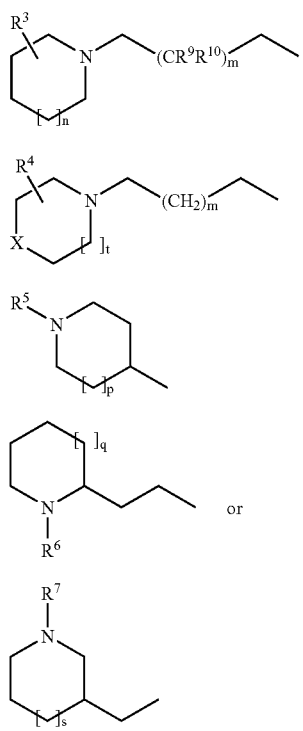

wherein
m is 0, 1 or 2;
n is 0, 1 or 2;
$R^3$ is hydrogen or lower alkyl;
$R^9$ and $R^{10}$ are independently from each other selected from hydrogen or lower alkyl;
t is 1 or 2;
$R^4$ is hydrogen or lower alkyl;
X is O, S or N—$R^8$; with $R^8$ being hydrogen or lower alkyl;
p is 0, 1 or 2;
$R^5$ is lower alkyl or cycloalkyl;
q is 0, 1 or 2;
$R^6$ is lower alkyl;
s is 0, 1 or 2;
$R^7$ is lower alkyl;
and pharmaceutically acceptable salts thereof.

The invention also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In another embodiment, the invention relates to a method for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. A method for the treatment and/or prevention of obesity is preferred.

DETAILED DESCRIPTION

The compounds of formula I and their pharmaceutically acceptable salts possess valuable pharmacological properties. Specifically, it has been found that the compounds of the present invention are histamine 3 receptor (H3R) antagonists and/or inverse agonists.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl, cyclopentyl and cyclohexyl.

The term "lower cycloalkylalkyl" or "$C_{3-7}$-cycloalkyl-$C_{1-8}$- alkyl" refers to lower alkyl groups as defined above wherein at least one of the hydrogen atoms of the lower alkyl group is replaced by cycloalkyl. A preferred example is cyclopropylmethyl.

The term "alkoxy" refers to the group R'—O—, wherein R' is alkyl. The term "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfanylethyl.

The term "halogen" refers to fluorine, chlorine, bromine and iodine, with fluorine, chlorine and bromine being preferred.

The term "lower halogenalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkyl" or hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "carbamoyl" refers to the group —CO—NH$_2$.

The term "lower halogenalkylcarbonylamino" refers to the group —NH—CO-lower halogenalkyl, wherein "lower halogenalkyl" has the previously given significance.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are thienyl and pyridyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiamorpholinyl. Preferred heterocyclyl groups are piperidinyl, morpholinyl and pyrrolidinyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "form a 4-, 5-, 6- or 7-membered saturated heterocyclic ring optionally containing a further heteroatom selected from nitrogen, oxygen or sulfur" refers to a saturated N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered partly unsaturated heterocyclic ring" means a heterocyclic ring as defined above which contains a double bond, for example 2,5-dihydropyrrolyl or 3,6-dihydro-2H-pyridinyl. The heteroyclic ring may be unsubstituted or substituted by one, two or three groups independently selected from lower alkyl, lower alkoxy and oxo. The heterocyclic ring may also be condensed with a phenyl ring, said phenyl ring being unsubstituted or substituted by one, two or three groups independently selected from lower alkyl, lower alkoxy and halogen. An example for such a condensed heterocyclic ring is 3,4-dihydro-1H-isoquinoline.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

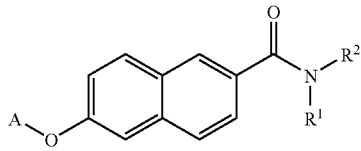

I wherein
R$^1$ is selected from the group consisting of hydrogen,
lower alkyl,
phenyl unsubstituted or substituted with one or two groups independently selected from the group consisting of lower alkyl, lower halogenalkoxy and lower hydroxyalkyl,
lower phenylalkyl, wherein the phenyl ring is unsubstituted or substituted with one or two groups independently selected from the group consisting of lower alkyl, halogen, lower alkoxy and lower hydroxyalkyl, and
lower alkoxyalkyl;

R$^2$ is selected from the group consisting of hydrogen,
lower alkyl,
cycloalkyl,
lower cycloalkylalkyl,
lower hydroxyalkyl,
lower alkoxyalkyl,
lower alkylsulfanylalkyl,
lower dialkylaminoalkyl,
phenyl unsubstituted or substituted with one or two groups independently selected from the group consisting of lower alkyl, halogen, lower alkoxy and lower hydroxyalkyl,
lower phenylalkyl, wherein the phenyl ring is unsubstituted or substituted with one or two groups independently selected from the group consisting of lower alkyl, halogen, lower alkoxy and lower hydroxyalkyl,
pyrrolidinyl unsubstituted or substituted with a group selected lower alkyl or halogen,
lower heteroarylalkyl, wherein the heteroaryl ring is unsubstituted or substituted with one or two lower alkyl groups, and
lower heterocyclylalkyl, wherein the heterocyclyl ring is unsubstituted or substituted with one or two lower alkyl groups; or
R$^1$ and R$^2$ together with the nitrogen atom to which they are attached form a 4-, 5-, 6- or 7-membered saturated or partly unsaturated heterocyclic ring optionally containing a further heteroatom selected from nitrogen, oxygen or sulfur,
said saturated heterocyclic ring
being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or
being condensed with a phenyl ring, said phenyl ring being unsubstituted or substituted by one, two or three groups independently selected from lower alkyl, lower alkoxy and halogen;
A is selected from

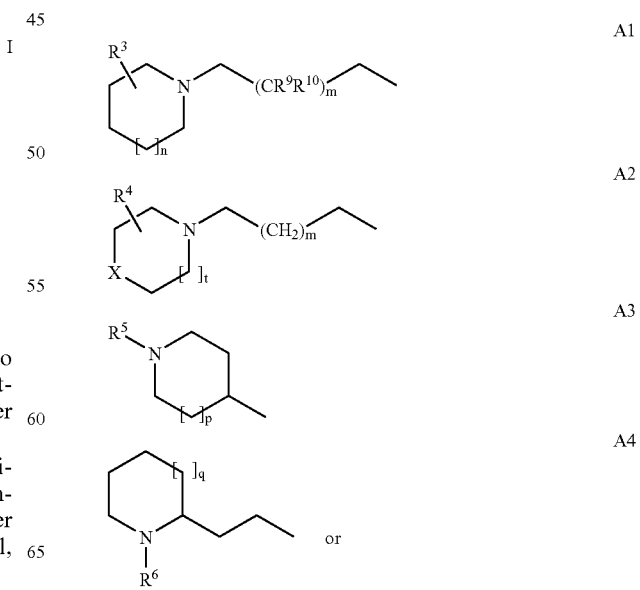

-continued

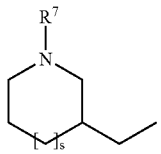
A5 wherein
m is 0, 1 or 2;
n is 0, 1 or 2;
$R^3$ is hydrogen or lower alkyl;
$R^9$ and $R^{10}$ are independently from each other selected from hydrogen or lower alkyl;
t is 1 or 2;
$R^4$ is hydrogen or lower alkyl;
X is O, S or N—$R^8$; with $R^8$ being hydrogen or lower alkyl;
p is 0, 1 or 2;
$R^5$ is lower alkyl or cycloalkyl;
q is 0, 1 or 2;
$R^6$ is lower alkyl;
s is 0, 1 or 2;
$R^7$ is lower alkyl;
and pharmaceutically acceptable salts thereof.

In one embodiment, the present invention relates to compounds of formula I according to the invention, wherein
$R^1$ is selected from the group consisting of hydrogen,
lower alkyl,
phenyl unsubstituted or substituted with one or two groups independently selected from lower alkyl, lower halogenalkoxy or lower hydroxyalkyl, and
lower phenylalkyl wherein the phenyl ring may be unsubstituted or substituted with one or two groups independently selected from lower alkyl, halogen, lower alkoxy or lower hydroxyalkyl;
$R^2$ is selected from the group consisting of hydrogen,
lower alkyl,
phenyl unsubstituted or substituted with one or two groups independently selected from lower alkyl, halogen, lower alkoxy or lower hydroxyalkyl, and
lower phenylalkyl wherein the phenyl ring may be unsubstituted or substituted with one or two groups independently selected from lower alkyl, halogen, lower alkoxy or lower hydroxyalkyl; or
$R^1$ and $R^2$ together with the nitrogen atom to which they are attached form a 5-or 6-membered saturated heterocyclic ring optionally containing a further heteroatom selected from nitrogen, oxygen or sulfur, said saturated heterocyclic ring being unsubstituted or substituted by one, two or three groups independently selected from lower alkyl, lower alkoxy and oxo, or being condensed with a phenyl ring, said phenyl ring being unsubstituted or substituted by one, two or three groups independently selected from lower alkyl, lower alkoxy and halogen;
A is selected from

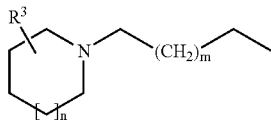
A1'

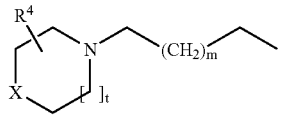
A2

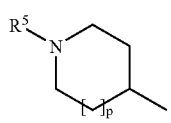
A3

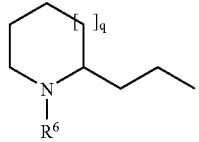
A4 or

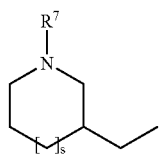
A5 wherein
m is 0, 1 or 2;
n is 0, 1 or 2;
$R^3$ is hydrogen or lower alkyl;
t is 1 or 2;
$R^4$ is hydrogen or lower alkyl;
X is O, S or N—$R^8$; with $R^8$ being hydrogen or lower alkyl;
p is 0, 1 or 2;
$R^5$ is lower alkyl;
q is 0, 1 or 2;
$R^6$ is lower alkyl;
s is 0, 1 or 2;
$R^7$ is lower alkyl;
and pharmaceutically acceptable salts thereof.

Preferred compounds of formula I of the present invention are compounds of formula I, wherein $R^1$ is is selected from the group consisting of hydrogen, lower alkyl, phenyl unsubstituted or substituted with one or two groups independently selected from lower alkyl, lower halogenalkoxy or lower hydroxyalkyl, and lower phenylalkyl wherein the phenyl ring may be unsubstituted or substituted with one or two groups independently selected from lower alkyl, halogen, lower alkoxy or lower hydroxyalkyl and $R^2$ is hydrogen or lower alkyl. Especially preferred are compounds of formula I, wherein $R^1$ is lower phenylalkyl wherein the phenyl ring may be unsubstituted or substituted with one or two groups independently selected from lower alkyl, halogen, lower alkoxy or lower hydroxyalkyl and and $R^2$ is hydrogen or lower alkyl.

Furthermore, compounds of formula I of the present invention are preferred, wherein
$R^2$ is selected from the group consisting of
hydrogen, lower alkyl, cycloalkyl, lower cycloalkylalkyl, lower hydroxyalkyl,
lower alkoxyalkyl, lower alkylsulfanylalkyl, lower dialkylaminoalkyl,
phenyl unsubstituted or substituted with one or two groups independently selected from the group consisting of lower alkyl, halogen, lower alkoxy and lower hydroxyalkyl, lower phenylalkyl, wherein the phenyl ring is unsubstituted or substituted with one or two groups independently selected from the group consisting of lower alkyl, halogen, lower alkoxy and lower hydroxyalkyl, pyrrolidinyl unsubstituted or substituted with a group selected lower alkyl or halogen, lower heteroarylalkyl, wherein the heteroaryl ring is unsubstituted or substituted with one or two lower alkyl groups, and lower heterocyclylalkyl, wherein the heterocyclyl ring is unsubstituted or substituted with one or two lower alkyl groups.

Especially preferred are those compounds of formula I, wherein $R^2$ is selected from the group consisting of hydrogen, lower alkyl, phenyl unsubstituted or substituted with one or two groups independently selected from the group consisting of lower alkyl, halogen, lower alkoxy and lower hydroxyalkyl, lower phenylalkyl, wherein the phenyl ring is unsubstituted or substituted with one or two groups independently selected from the group consisting of lower alkyl, halogen, lower alkoxy and lower hydroxyalkyl, and pyrrolidinyl unsubstituted or substituted with a group selected lower alkyl or halogen.

Another group of preferred compounds of formula I according to the invention are those, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen.

Especially preferred are those compounds of formula I, wherein $R^1$ and $R^2$ together with the nitrogen atom to which they are attached form a heterocyclic ring selected from the group consisting of piperidine, piperazine, pyrrolidine, thiomorpholine, morpholine and azepane, said heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen.

Further preferred compounds of formula I are those compounds, wherein $R^1$ and $R^2$ together with the nitrogen atom to which they are attached form a 5- or 6-membered saturated heterocyclic ring optionally containing a further heteroatom selected from nitrogen, oxygen or sulfur, said saturated heterocyclic ring being unsubstituted or substituted by one, two or three groups independently selected from lower alkyl, lower alkoxy and oxo, or being condensed with a phenyl ring, said phenyl ring being unsubstituted or substituted by one, two or three groups independently selected from lower alkyl, lower alkoxy and halogen.

Within this group those compounds of formula I are preferred, wherein $R^1$ and $R^2$ together with the nitrogen atom to which they are attached form a heterocyclic ring selected from the group consisting of piperidine, piperazine, pyrrolidine, thiomorpholine and morpholine, said heterocyclic ring being unsubstituted or substituted by one, two or three groups independently selected from lower alkyl, lower alkoxy and oxo, or being condensed with a phenyl ring, said phenyl ring being unsubstituted or substituted by one, two or three groups independently selected from lower alkyl, lower alkoxy and halogen.

Even more preferably, $R^1$ and $R^2$ together with the nitrogen atom to which they are attached form a saturated heterocyclic ring selected from the group consisting of piperidine, piperazine, pyrrolidine and 3,4-dihydro-1H-isoquinoline, wherein the ring is unsubstituted or substituted by lower alkyl.

Further preferred compounds of formula I according to the present invention are those, wherein A signifies

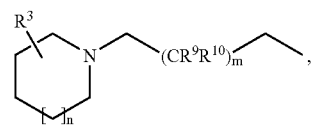

wherein m is 0, 1 or 2; n is 0, 1 or 2; $R^3$ is hydrogen or lower alkyl, and $R^9$ and $R^{10}$ are independently from each other selected from hydrogen or lower alkyl.

Especially preferred are those compounds, wherein $R^9$ and $R^{10}$ are hydrogen, meaning compounds of formula I, wherein A signifies

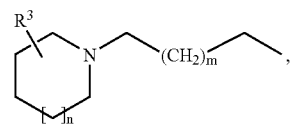

wherein m is 0, 1 or 2; n is 0, 1 or 2; and $R^3$ is hydrogen or lower alkyl.

Within this group, those compounds of formula I are preferred, wherein m is 1 and n is 1, thus meaning piperidine groups are preferred.

Another preferred group of compounds are those compounds of formula I, wherein A signifies

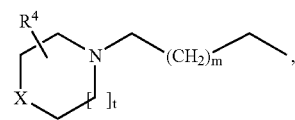

wherein m is 0, 1 or 2; t is 1 or 2; $R^4$ is hydrogen or lower alkyl; and X is O, S or N—$R^8$; with $R^8$ being hydrogen or lower alkyl, with those compounds, wherein t is 1 and X is O, thus meaning morpholine derivatives, being more preferred, and those compounds, wherein m is 1, being even more preferred.

Furthermore, compounds of formula I according to the invention, wherein A signifies

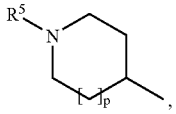
A3 wherein p is 0, 1 or 2 and R⁵ is lower alkyl or cycloalkyl, are also preferred. Especially preferred are those compounds of formula I, wherein R⁵ is lower alkyl. Within this group, compounds of formula I, wherein p is 0 or wherein p is 1, are especially preferred, thus meaning pyrrolidine or piperidine groups being especially preferred.

Compounds of formula I according to the present invention, wherein A signifies

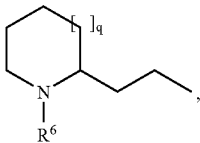
A4 wherein q is 0, 1 or 2; and R⁶ is lower alkyl, are also preferred. Within this group, compounds of formula I, wherein q is 0, are preferred. Thus meaning, pyrrolidine groups are preferred.

Also preferred are those compounds of formula I, wherein q is 1, thus meaning piperidine groups are also preferred.

Another group of preferred compounds are those compounds of formula I, wherein A signifies

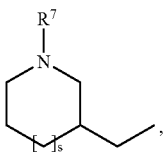
A5 wherein s is 0, 1 or 2; and R⁷ is lower alkyl.

Especially preferred are those compounds of formula I, wherein s is 1. Thus meaning piperidine groups are preferred.

Examples of preferred compounds of formula I are the following:
piperidin-1-yl-[6-(3-piperidin-1-yl-propoxy)-naphthalen-2-yl]-methanone,
(4-methyl-piperidin-1-yl)-[6-(3-piperidin-1-yl-propoxy)-naphthalen-2-yl]-methanone;
(4-methyl-piperidin-1-yl)-{6-[3-(2-methyl-piperidin-1-yl)-propoxy]-naphthalen-2-yl}-methanone,
(4-isopropyl-piperazin-1-yl)-[6-(3-piperidin-1-yl-propoxy)-naphthalen-2-yl]-methanone,
(4-isopropyl-piperazin-1-yl)-{6-[2-(1-methyl-piperidin-2-yl)-ethoxy]-naphthalen-2-yl}-methanone,
(2-methyl-pyrrolidin-1-yl)-[6-(3-piperidin-1-yl-propoxy)-naphthalen-2-yl]-methanone,
{6-[3-(2-methyl-piperidin-1-yl)-propoxy]-naphthalen-2-yl}-(2-methyl-pyrrolidin-1-yl)-methanone,
{6-[2-(1-methyl-piperidin-2-yl)-ethoxy]-naphthalen-2-yl}-(2-methyl-pyrrolidin-1-yl)-methanone,
(3,4-dihydro-1H-isoquinolin-2-yl)-[6-(3-piperidin-1-yl-propoxy)-naphthalen-2-yl]-methanone,
(3,4-dihydro-1H-isoquinolin-2-yl)-{6-[3-(2-methyl-piperidin-1-yl)-propoxy]-naphthalen-2-yl}-methanone,
(3,4-dihydro-1H-isoquinolin-2-yl)-{6-[2-(1-methyl-piperidin-2-yl)-ethoxy]-naphthalen-2-yl}-methanone,
6-(3-piperidin-1-yl-propoxy)-naphthalene-2-carboxylic acid benzyl-methyl-amide,
6-[3-(2-methyl-piperidin-1-yl)-propoxy]-naphthalene-2-carboxylic acid benzyl-methyl-amide,
[6-(3-piperidin-1-yl-propoxy)-naphthalen-2-yl]-thiomorpholin-4-yl-methanone,
[6-(3-morpholin-4-yl-propoxy)-naphthalen-2-yl]-thiomorpholin-4-yl-methanone,
{6-[3-(2-methyl-piperidin-1-yl)-propoxy]-naphthalen-2-yl}-thiomorpholin-4-yl-methanone,
{6-[2-(1-methyl-piperidin-2-yl)-ethoxy]-naphthalen-2-yl}-thiomorpholin-4-yl-methanone,
(4-methoxy-piperidin-1-yl)-[6-(3-piperidin-1-yl-propoxy)-naphthalen-2-yl]-methanone,
(4-methoxy-piperidin-1-yl)-{6-[3-(2-methyl-piperidin-1-yl)-propoxy]-naphthalen-2-yl}-methanone,
(4-methoxy-piperidin-1-yl)-{6-[2-(1-methyl-piperidin-2-yl)-ethoxy]-naphthalen-2-yl}-methanone,
6-(3-piperidin-1-yl-propoxy)-naphthalene-2-carboxylic acid 3-methoxy-benzylamide,
6-[3-(2-methyl-piperidin-1-yl)-propoxy]-naphthalene-2-carboxylic acid 3-methoxy-benzylamide,
morpholin-4-yl-[6-(3-morpholin-4-yl-propoxy)-naphthalen-2-yl]-methanone,
{6-[3-(2-methyl-piperidin-1-yl)-propoxy]-naphthalen-2-yl}-morpholin-4-yl-methanone,
{6-[2-(1-methyl-piperidin-2-yl)-ethoxy]-naphthalen-2-yl}-morpholin-4-yl-methanone,
[6-(3-piperidin-1-yl-propoxy)-naphthalen-2-yl]-pyrrolidin-1-yl-methanone,
{6-[3-(2-methyl-piperidin-1-yl)-propoxy]-naphthalen-2-yl}-pyrrolidin-1-yl-methanone,
{6-[2-(1-methyl-pyrrolidin-2-yl)-ethoxy]-naphthalen-2-yl}-piperidin-1-yl-methanone,
[6-(1-isopropyl-pyrrolidin-3-yloxy)-naphthalen-2-yl]-piperidin-1-yl-methanone,
[6-(1-isobutyl-piperidin-4-yloxy)-naphthalen-2-yl]-piperidin-1-yl-methanone,
(4-methyl-piperidin-1-yl)-{6-[2-(1-methyl-pyrrolidin-2-yl)-ethoxy]-naphthalen-2-yl}-methanone,
[6-(1-isopropyl-pyrrolidin-3-yloxy)-naphthalen-2-yl]-(4-methyl-piperidin-1-yl)-methanone,
[6-(1-isopropyl-piperidin-4-yloxy)-naphthalen-2-yl]-(4-methyl-piperidin-1-yl)-methanone,
[6-(1-isobutyl-piperidin-4-yloxy)-naphthalen-2-yl]-(4-methyl-piperidin-1-yl) -methanone,
(2-methyl-pyrrolidin-1-yl)-{6-[2-(1-methyl-pyrrolidin-2-yl)-ethoxy]-naphthalen-2-yl}-methanone,
[6-(1-isopropyl-pyrrolidin-3-yloxy)-naphthalen-2-yl]-(2-methyl-pyrrolidin-1-yl)-methanone,
[6-(1-isopropyl-piperidin-4-yloxy)-naphthalen-2-yl]-(2-methyl-pyrrolidin-1-yl)-methanone,
[6-(1-isobutyl-piperidin-4-yloxy)-naphthalen-2-yl]-(2-methyl-pyrrolidin-1-yl)-methanone,
(3,4-dihydro-1H-isoquinolin-2-yl)-{6-[2-(1-methyl-pyrrolidin-2-yl)-ethoxy]-naphthalen-2-yl}-methanone, (3,4-dihydro-1H-isoquinolin-2-yl)-[6-(1-isopropyl-pyrrolidin-3-yloxy)-naphthalen-2-yl]-methanone,
(3,4-dihydro-1H-isoquinolin-2-yl)-[6-(1-isopropyl-piperidin-4-yloxy)-naphthalen-2-yl]-methanone,
(3,4-dihydro-1H-isoquinolin-2-yl)-[6-(1-isobutyl-piperidin-4-yloxy)-naphthalen-2-yl]-methanone,
(3,4-dihydro-1H-isoquinolin-2-yl)-[6-(1-methyl-piperidin-3-ylmethoxy)-naphthalen-2-yl]-methanone,
6-[2-(1-methyl-pyrrolidin-2-yl)-ethoxy]-naphthalene-2-carboxylic acid benzyl-methyl-amide,
6-(1-isopropyl-pyrrolidin-3-yloxy)-naphthalene-2-carboxylic acid benzyl-methyl-amide,
6-(1-isopropyl-piperidin-4-yloxy)-naphthalene-2-carboxylic acid benzyl-methyl-amide,
6-(1-isobutyl-piperidin-4-yloxy)-naphthalene-2-carboxylic acid benzyl-methyl-amide,
{6-[2-(1-methyl-pyrrolidin-2-yl)-ethoxy]-naphthalen-2-yl}-thiomorpholin-4-yl-methanone,
[6-(1-isopropyl-pyrrolidin-3-yloxy)-naphthalen-2-yl]-thiomorpholin-4-yl-methanone,
[6-(1-isopropyl-piperidin-4-yloxy)-naphthalen-2-yl]-thiomorpholin-4-yl-methanone,
[6-(1-isobutyl-piperidin-4-yloxy)-naphthalen-2-yl]-thiomorpholin-4-yl-methanone,
(4-methoxy-piperidin-1-yl)-{6-[2-(1-methyl-pyrrolidin-2-yl)-ethoxy]-naphthalen-2-yl}-methanone,
[6-(1-isopropyl-pyrrolidin-3-yloxy)-naphthalen-2-yl]-(4-methoxy-piperidin-1-yl)-methanone,
[6-(1-isopropyl-piperidin-4-yloxy)-naphthalen-2-yl]-(4-methoxy-piperidin-1-yl)-methanone,
[6-(1-isobutyl-piperidin-4-yloxy)-naphthalen-2-yl]-(4-methoxy-piperidin-1-yl)-methanone,
6-[2-(1-methyl-pyrrolidin-2-yl)-ethoxy]-naphthalene-2-carboxylic acid 3-methoxy-benzylamide,
6-(1-isopropyl-pyrrolidin-3-yloxy)-naphthalene-2-carboxylic acid 3-methoxy-benzylamide,
6-(1-isopropyl-piperidin-4-yloxy)-naphthalene-2-carboxylic acid 3-methoxy-benzylamide,
6-(1-isobutyl-piperidin-4-yloxy)-naphthalene-2-carboxylic acid 3-methoxy-benzylamide,
6-(1-methyl-piperidin-3-ylmethoxy)-naphthalene-2-carboxylic acid 3-methoxy-benzylamide,
{6-[2-(1-methyl-pyrrolidin-2-yl)-ethoxy]-naphthalen-2-yl}-morpholin-4-yl-methanone,
[6-(1-isopropyl-pyrrolidin-3-yloxy)-naphthalen-2-yl]-morpholin-4-yl-methanone,
[6-(1-isopropyl-piperidin-4-yloxy)-naphthalen-2-yl]-morpholin-4-yl-methanone,
[6-(1-isobutyl-piperidin-4-yloxy)-naphthalen-2-yl]-morpholin-4-yl-methanone 1:1 hydrochloride,
{6-[2-(1-methyl-pyrrolidin-2-yl)-ethoxy]-naphthalen-2-yl}-pyrrolidin-1-yl-methanone,
[6-(1-isopropyl-pyrrolidin-3-yloxy)-naphthalen-2-yl]-pyrrolidin-1-yl-methanone,
[6-(1-isopropyl-piperidin-4-yloxy)-naphthalen-2-yl]-pyrrolidin-1-yl-methanone,
[6-(1-isobutyl-piperidin-4-yloxy)-naphthalen-2-yl]-pyrrolidin-1-yl-methanone,
(4-isopropyl-piperazin-1-yl)-{6-[2-(1-methyl-pyrrolidin-2-yl)-ethoxy]-naphthalen-2-yl}-methanone,
(4-isopropyl-piperazin-1-yl)-[6-(1-isopropyl-pyrrolidin-3-yloxy)-naphthalen-2-yl]-methanone,
[6-(1-isobutyl-piperidin-4-yloxy)-naphthalen-2-yl]-(4-isopropyl-piperazin-1-yl)-methanone,
(4-isopropyl-piperazin-1-yl)-[6-(1-methyl-piperidin-3-ylmethoxy)-naphthalen-2-yl]-methanone,
[6-(1-isopropyl-piperidin-4-yloxy)-naphthalen-2-yl]-piperidin-1-yl-methanone 1:1 hydrochloride,
(1,1-dioxo-6-thiomorpholin-4-yl)-[6-(1-isopropyl-piperidin-4-yloxy)-naphthalen-2-yl]-methanone 1:1 hydrochloride,
[6-(2,2-dimethyl-3-piperidin-1-yl-propoxy)-naphthalen-2-yl]-(4-methyl-piperidin-1-yl)-methanone,
6-(3-piperidin-1-yl-propoxy)-naphthalene-2-carboxylic acid ethylamide 1:1 hydrochloride,
6-(3-piperidin-1-yl-propoxy)-naphthalene-2-carboxylic acid ethyl-methyl-amide 1:1 hydrochloride,
(4,4-difluoro-piperidin-1-yl)-[6-(3-piperidin-1-yl-propoxy)-naphthalen-2-yl]-methanone 1:1 hydrochloride,
(2,6-dimethyl-morpholin-4-yl)-[6-(3-piperidin-1-yl-propoxy)-naphthalen-2-yl]-methanone 1:1 hydrochloride,
6-(3-piperidin-1-yl-propoxy)-naphthalene-2-carboxylic acid methyl-phenethyl-amide 1:1 hydrochloride,
6-(3-piperidin-1-yl-propoxy)-naphthalene-2-carboxylic acid propylamide 1:1 hydrochloride,
6-(3-piperidin-1-yl-propoxy)-naphthalene-2-carboxylic acid methyl-propyl-amide 1:1 hydrochloride,
6-(3-piperidin-1-yl-propoxy)-naphthalene-2-carboxylic acid ethyl-propyl-amide 1:1 hydrochloride,
6-(3-piperidin-1-yl-propoxy)-naphthalene-2-carboxylic acid cyclohexyl-methyl-amide 1:1 hydrochloride,
(3-hydroxy-pyrrolidin-1-yl)-[6-(3-piperidin-1-yl-propoxy)-naphthalen-2-yl]-methanone 1:1 hydrochloride,
6-(3-piperidin-1-yl-propoxy)-naphthalene-2-carboxylic acid benzyl-isopropyl-amide 1:1 hydrochloride,
6-(3-piperidin-1-yl-propoxy)-naphthalene-2-carboxylic acid butylamide 1:1 hydrochloride,
azetidin-1-yl-[6-(3-piperidin-1-yl-propoxy)-naphthalen-2-yl]-methanone 1:1 hydrochloride,
azepan-1-yl-[6-(3-piperidin-1-yl-propoxy)-naphthalen-2-yl]-methanone 1:1 hydrochloride,
6-(3-piperidin-1-yl-propoxy)-naphthalene-2-carboxylic acid ethyl-(2-methoxy-ethyl)-amide 1:1 hydrochloride,
6-(3-piperidin-1-yl-propoxy)-naphthalene-2-carboxylic acid cyclopropylmethyl-amide 1:1 hydrochloride,
6-(3-piperidin-1-yl-propoxy)-naphthalene-2-carboxylic acid ethyl-isopropyl-amide 1:1 hydrochloride,
6-(3-piperidin-1-yl-propoxy)-naphthalene-2-carboxylic acid bis-(2-methoxy-ethyl)-amide 1:1 hydrochloride,
(3-methoxy-piperidin-1-yl)-[6-(3-piperidin-1-yl-propoxy)-naphthalen-2-yl]-methanone 1:1 hydrochloride,
(4-hydroxymethyl-piperidin-1-yl)-[6-(3-piperidin-1-yl-propoxy)-naphthalen-2-yl]-methanone 1:1 hydrochloride,
6-(3-piperidin-1-yl-propoxy)-naphthalene-2-carboxylic acid isobutyl-amide 1:1 hydrochloride,
6-(3-piperidin-1-yl-propoxy)-naphthalene-2-carboxylic acid cyclohexyl-ethyl-amide 1:1 hydrochloride,
6-(3-piperidin-1-yl-propoxy)-naphthalene-2-carboxylic acid cyclopropylamide 1:1 hydrochloride,
6-(3-piperidin-1-yl-propoxy)-naphthalene-2-carboxylic acid (2-methoxy-ethyl)-amide 1:1 hydrochloride,
6-(3-piperidin-1-yl-propoxy)-naphthalene-2-carboxylic acid [2-(3,4-dimethoxy-phenyl)-ethyl]-methyl-amide 1:1 hydrochloride,
6-(3-piperidin-1-yl-propoxy)-naphthalene-2-carboxylic acid ethyl-(2-fluoro-benzyl)-amide 1:1 hydrochloride,
(2-methyl-piperidin-1-yl)-[6-(3-piperidin-1-yl-propoxy)-naphthalen-2-yl]-methanone 1:1 hydrochloride,
(4-benzyl-piperazin-1-yl)-[6-(3-piperidin-1-yl-propoxy)-naphthalen-2-yl]-methanone 1:2 hydrochloride,
(3-methyl-piperidin-1-yl)-[6-(3-piperidin-1-yl-propoxy)-naphthalen-2-yl]-methanone 1:1 hydrochloride, 6-(3-piperidin-1-yl-propoxy)-naphthalene-2-carboxylic acid ethyl-pyridin-4-ylmethyl-amide 1:1 hydrochloride,
6-(3-piperidin-1-yl-propoxy)-naphthalene-2-carboxylic acid cyclobutylamide 1:1 hydrochloride,
(4-phenyl-piperazin-1-yl)-[6-(3-piperidin-1-yl-propoxy)-naphthalen-2-yl]-methanone 1:2 hydrochloride,
6-(3-piperidin-1-yl-propoxy)-naphthalene-2-carboxylic acid (2-thiophen-2-yl-ethyl)-amide 1:1 hydrochloride,
6-(3-piperidin-1-yl-propoxy)-naphthalene-2-carboxylic acid (3-methoxy-propyl)-amide 1:1 hydrochloride,
6-(3-piperidin-1-yl-propoxy)-naphthalene-2-carboxylic acid (3-methyl-thiophen-2-ylmethyl)-amide 1:1 hydrochloride,
6-(3-piperidin-1-yl-propoxy)-naphthalene-2-carboxylic acid [2-(2-methyl-piperidin-1-yl)-ethyl]-amide 1:2 hydrochloride,
(1,3-dihydro-isoindol-2-yl)-[6-(3-piperidin-1-yl-propoxy)-naphthalen-2-yl]-methanone 1:1 hydrochloride,
6-(3-piperidin-1-yl-propoxy)-naphthalene-2-carboxylic acid (2-morpholin-4-yl-ethyl)-amide 1:2 hydrochloride,
6-(3-piperidin-1-yl-propoxy)-naphthalene-2-carboxylic acid (thiophen-2-ylmethyl)-amide 1:1 hydrochloride,
(3,6-dihydro-2H-pyridin-1-yl)-[6-(3-piperidin-1-yl-propoxy)-naphthalen-2-yl]-methanone 1:1 hydrochloride,
[6-(3-piperidin-1-yl-propoxy)-naphthalen-2-yl]-(3-pyridin-2-yl-pyrrolidin-1-yl)-methanone 1:1 hydrochloride,
6-(3-piperidin-1-yl-propoxy)-naphthalene-2-carboxylic acid (2-dimethylamino-ethyl)-ethyl-amide 1:2 hydrochloride,
(4-fluoro-piperidin-1-yl)-[6-(3-piperidin-1-yl-propoxy)-naphthalen-2-yl]-methanone; 1:1 hydrochloride,
(4-benzyl-piperidin-1-yl)-[6-(3-piperidin-1-yl-propoxy)-naphthalen-2-yl]-methanone 1:1 hydrochloride,
(4-methyl-piperazin-1-yl)-[6-(3-piperidin-1-yl-propoxy)-naphthalen-2-yl]-methanone 1:2 hydrochloride,
6-(3-piperidin-1-yl-propoxy)-naphthalene-2-carboxylic acid cycloheptylamide 1:1 hydrochloride,
6-(3-piperidin-1-yl-propoxy)-naphthalene-2-carboxylic acid cyclopentylamide 1:1 hydrochloride,
(4-hydroxy-piperidin-1-yl)-[6-(3-piperidin-1-yl-propoxy)-naphthalen-2-yl]-methanone 1:1 hydrochloride,
1-[6-(3-piperidin-1-yl-propoxy)-naphthalene-2-carbonyl]-piperidine-4-carboxylic acid amide 1:1 hydrochloride,
(3-hydroxymethyl-piperidin-1-yl)-[6-(3-piperidin-1-yl-propoxy)-naphthalen-2-yl]-methanone 1:1 hydrochloride,
6-(3-piperidin-1-yl-propoxy)-naphthalene-2-carboxylic acid cyclohexylamide 1:1 hydrochloride;
(4-bromo-piperidin-1-yl)-[6-(3-piperidin-1-yl-propoxy)-naphthalen-2-yl]-methanone 1:1 hydrochloride,
(4-benzyl-4-hydroxy-piperidin-1-yl)-[6-(3-piperidin-1-yl-propoxy)-naphthalen-2-yl]-methanone 1:1 hydrochloride,
6-(3-piperidin-1-yl-propoxy)-naphthalene-2-carboxylic acid [3-(1-hydroxy-ethyl)-phenyl]-amide 1:1 hydrochloride,
(3-methanesulfonyl-pyrrolidin-1-yl)-[6-(3-piperidin-1-yl-propoxy)-naphthalen-2-yl]-methanone 1:1 hydrochloride,
(2-isopropyl-pyrrolidin-1-yl)-[6-(3-piperidin-1-yl-propoxy)-naphthalen-2-yl]-methanone 1:1 hydrochloride,
6-(3-piperidin-1-yl-propoxy)-naphthalene-2-carboxylic acid (3,4-dimethyl-phenyl)-amide 1:1 hydrochloride,
(3-dimethylamino-pyrrolidin-1-yl)-[6-(3-piperidin-1-yl-propoxy)-naphthalen-2-yl]-methanone 1:2 hydrochloride,
2,2,2-trifluoro-N-{1-[6-(3-piperidin-1-yl-propoxy)-naphthalene-2-carbonyl]-pyrrolidin-3-yl}-acetamide 1:1 hydrochloride,
6-(3-piperidin-1-yl-propoxy)-naphthalene-2-carboxylic acid methyl-(1-methyl-pyrrolidin-3-yl)-amide 1:2 hydrochloride,
[6-(3-piperidin-1-yl-propoxy)-naphthalen-2-yl]-(4-trifluoromethyl-piperidin-1-yl)-methanone 1:1 hydrochloride,
[6-(1-isopropyl-piperidin-4-yloxy)-naphthalen-2-yl]-(4-methyl-piperazin-1-yl)-methanone 1:2 hydrochloride,
[6-(1-isopropyl-piperidin-4-yloxy)-naphthalen-2-yl]-(2-isopropyl-pyrrolidin-1-yl)-methanone 1:1 hydrochloride,
(4-benzyl-piperidin-1-yl)-[6-(1-isopropyl-piperidin-4-yloxy)-naphthalen-2-yl]-methanone 1:1 hydrochloride,
(4-isopropyl-piperazin-1-yl)-[6-(1-isopropyl-piperidin-4-yloxy)-naphthalen-2-yl]-methanone 1:2 hydrochloride,
(4-hydroxymethyl-piperidin-1-yl)-[6-(1-isopropyl-piperidin-4-yloxy)-naphthalen-2-yl]-methanone 1:1 hydrochloride,
6-(1-isopropyl-piperidin-4-yloxy)-naphthalene-2-carboxylic acid (2-methoxy-ethyl)-amide 1:1 hydrochloride,
6-(1-isopropyl-piperidin-4-yloxy)-naphthalene-2-carboxylic acid 4-methyl-benzylamide 1:1 hydrochloride,
[6-(1-isopropyl-piperidin-4-yloxy)-naphthalen-2-yl]-(4-trifluoromethyl-piperidin-1-yl)-methanone 1:1 hydrochloride,
(4-fluoro-piperidin-1-yl)-[6-(1-isopropyl-piperidin-4-yloxy)-naphthalen-2-yl]-methanone 1:1 hydrochloride,
(4,4-difluoro-piperidin-1-yl)-[6-(1-isopropyl-piperidin-4-yloxy)-naphthalen-2-yl]-methanone 1:1 hydrochloride,
6-(1-isopropyl-piperidin-4-yloxy)-naphthalene-2-carboxylic acid cyclopropylmethyl-amide 1:1 hydrochloride,
6-(1-isopropyl-piperidin-4-yloxy)-naphthalene-2-carboxylic acid (2-methylsulfanyl-ethyl)-amide 1:1 hydrochloride,
6-(1-isopropyl-piperidin-4-yloxy)-naphthalene-2-carboxylic acid 4-fluoro-benzylamide 1:1 hydrochloride,
[6-(1-isopropyl-piperidin-4-yloxy)-naphthalen-2-yl]-(3-methoxy-piperidin-1-yl)-methanone 1:1 hydrochloride,
6-(1-isopropyl-piperidin-4-yloxy)-naphthalene-2-carboxylic acid phenethyl-amide; 1:1 hydrochloride,
(3-hydroxy-pyrrolidin-1-yl)-[6-(1-isopropyl-piperidin-4-yloxy)-naphthalen-2-yl]-methanone 1:1 hydrochloride,
(4-hydroxy-piperidin-1-yl)-[6-(1-isopropyl-piperidin-4-yloxy)-naphthalen-2-yl]-methanone 1:1 hydrochloride,
6-(1-isopropyl-piperidin-4-yloxy)-naphthalene-2-carboxylic acid (3-dimethylamino-propyl)-amide 1:2 hydrochloride,
6-(1-isopropyl-piperidin-4-yloxy)-naphthalene-2-carboxylic acid ethyl-(2-methoxy-ethyl)-amide 1:1 hydrochloride,
6-(1-isopropyl-piperidin-4-yloxy)-naphthalene-2-carboxylic acid (2-morpholin-4-yl-ethyl)-amide 1:2 hydrochloride,
6-(1-isopropyl-piperidin-4-yloxy)-naphthalene-2-carboxylic acid (2-piperidin-1-yl-ethyl)-amide 1:2 hydrochloride,
(4-benzyl-piperazin-1-yl)-[6-(1-isopropyl-piperidin-4-yloxy)-naphthalen-2-yl]-methanone 1:2 hydrochloride,
6-(1-isopropyl-piperidin-4-yloxy)-naphthalene-2-carboxylic acid isopropyl-methyl-amide 1:1 hydrochloride,
azepan-1-yl-[6-(1-isopropyl-piperidin-4-yloxy)-naphthalen-2-yl]-methanone 1:1 hydrochloride,
6-(1-isopropyl-piperidin-4-yloxy)-naphthalene-2-carboxylic acid isobutyl-amide 1:1 hydrochloride,
6-(1-isopropyl-piperidin-4-yloxy)-naphthalene-2-carboxylic acid cyclohexyl-methyl-amide 1:1 hydrochloride,
6-(1-isopropyl-piperidin-4-yloxy)-naphthalene-2-carboxylic acid ethyl-pyridin-4-ylmethyl-amide 1:1 hydrochloride,
6-(1-isopropyl-piperidin-4-yloxy)-naphthalene-2-carboxylic acid methyl-phenethyl-amide 1:1 hydrochloride,
6-(1-isopropyl-piperidin-4-yloxy)-naphthalene-2-carboxylic acid methyl-propyl-amide 1:1 hydrochloride, 6-(1-isopropyl-piperidin-4-yloxy)-naphthalene-2-carboxylic acid cyclopropylmethyl-propyl-amide 1:1 hydrochloride,
6-(1-isopropyl-piperidin-4-yloxy)-naphthalene-2-carboxylic acid (3-methoxy-propyl)-amide 1:1 hydrochloride,
6-(1-isopropyl-piperidin-4-yloxy)-naphthalene-2-carboxylic acid propylamide 1:1 hydrochloride,
6-(1-isopropyl-piperidin-4-yloxy)-naphthalene-2-carboxylic acid cyclopentylamide 1:1 hydrochloride,
6-(1-isopropyl-piperidin-4-yloxy)-naphthalene-2-carboxylic acid cyclohexylamide 1:1 hydrochloride,
6-(1-isopropyl-piperidin-4-yloxy)-naphthalene-2-carboxylic acid ethyl-methyl-amide; 1:1 hydrochloride,
6-(1-isopropyl-piperidin-4-yloxy)-naphthalene-2-carboxylic acid tert-butylamide 1:1 hydrochloride,
6-(1-isopropyl-piperidin-4-yloxy)-naphthalene-2-carboxylic acid cyclopropylamide 1:1 hydrochloride,
6-(1-isopropyl-piperidin-4-yloxy)-naphthalene-2-carboxylic acid isopropylamide 1:1 hydrochloride,
6-(1-isopropyl-piperidin-4-yloxy)-naphthalene-2-carboxylic acid diethylamide 1:1 hydrochloride,
6-(1-isopropyl-piperidin-4-yloxy)-naphthalene-2-carboxylic acid methyl-(2-pyridin-2-yl-ethyl)-amide 1:1 hydrochloride,
6-(1-isopropyl-piperidin-4-yloxy)-naphthalene-2-carboxylic acid benzyl-ethyl-amide 1:1 hydrochloride,
[6-(1-isopropyl-piperidin-4-yloxy)-naphthalen-2-yl]-(2-methyl-piperidin-1-yl)-methanone 1:1 hydrochloride,
(3-dimethylamino-pyrrolidin-1-yl)-[6-(1-isopropyl-piperidin-4-yloxy)-naphthalen-2-yl]-methanone 1:2 hydrochloride,
6-(1-isopropyl-piperidin-4-yloxy)-naphthalene-2-carboxylic acid methyl-(1-methyl-pyrrolidin-3-yl)-amide 1:2 hydrochloride,
[6-(1-isopropyl-piperidin-4-yloxy)-naphthalen-2-yl]-(3-methanesulfonyl-pyrrolidin-1-yl)-methanone 1:1 hydrochloride,
6-(1-isopropyl-piperidin-4-yloxy)-naphthalene-2-carboxylic acid cycloheptylamide 1:1 hydrochloride,
2,2,2-trifluoro-N-{1-[6-(1-isopropyl-piperidin-4-yloxy)-naphthalene-2-carbonyl]-pyrrolidin-3-yl}-acetamide 1:1 hydrochloride,
1-[6-(1-isopropyl-piperidin-4-yloxy)-naphthalene-2-carbonyl]-piperidine-4-carboxylic acid amide 1:1 hydrochloride,
(4-cyclopentyl-piperazin-1-yl)-[6-(1-isopropyl-piperidin-4-yloxy)-naphthalen-2-yl]-methanone 1:2 hydrochloride,
[6-(1-isopropyl-piperidin-4-yloxy)-naphthalen-2-yl]-[4-(4-trifluoromethyl-phenyl)-piperazin-1-yl]-methanone 1:1 hydrochloride,
[6-(1-isopropyl-piperidin-4-yloxy)-naphthalen-2-yl]-((R)-2-methyl-pyrrolidin-1-yl)-methanone,
[6-(1-cyclopropyl-piperidin-4-yloxy)-naphthalen-2-yl]-morpholin-4-yl-methanone,
and pharmaceutically acceptable salts thereof.

Particularly preferred compounds of formula I of the present invention are the following:
piperidin-1-yl-[6-(3-piperidin-1-yl-propoxy)-naphthalen-2-yl]-methanone,
(4-methyl-piperidin-1-yl)-[6-(3-piperidin-1-yl-propoxy)-naphthalen-2-yl]-methanone,
(4-isopropyl-piperazin-1-yl)-[6-(3-piperidin-1-yl-propoxy)-naphthalen-2-yl]-methanone,
(4-isopropyl-piperazin-1-yl)-{6-[2-(1-methyl-piperidin-2-yl)-ethoxy]-naphthalen-2-yl}-methanone,
(2-methyl-pyrrolidin-1-yl)-[6-(3-piperidin-1-yl-propoxy)-naphthalen-2-yl]-methanone,
(3,4-dihydro-1H-isoquinolin-2-yl)-[6-(3-piperidin-1-yl-propoxy)-naphthalen-2-yl]-methanone,
(3,4-dihydro-1H-isoquinolin-2-yl)-{6-[3-(2-methyl-piperidin-1-yl)-propoxy]-naphthalen-2-yl}-methanone,
[6-(3-piperidin-1-yl-propoxy)-naphthalen-2-yl]-thiomorpholin-4-yl-methanone,
(4-methoxy-piperidin-1-yl)-[6-(3-piperidin-1-yl-propoxy)-naphthalen-2-yl]-methanone,
[6-(3-piperidin-1-yl-propoxy)-naphthalen-2-yl]-pyrrolidin-1-yl-methanone,
{6-[3-(2-methyl-piperidin-1-yl)-propoxy]-naphthalen-2-yl}-pyrrolidin-1-yl-methanone,
[6-(1-isopropyl-piperidin-4-yloxy)-naphthalen-2-yl]-(4-methyl-piperidin-1-yl)-methanone,
[6-(1-isopropyl-piperidin-4-yloxy)-naphthalen-2-yl]-(2-methyl-pyrrolidin-1-yl)-methanone,
(3,4-dihydro-1H-isoquinolin-2-yl)-{6-[2-(1-methyl-pyrrolidin-2-yl)-ethoxy]-naphthalen-2-yl}-methanone,
(3,4-dihydro-1H-isoquinolin-2-yl)-[6-(1-isopropyl-piperidin-4-yloxy)-naphthalen-2-yl]-methanone,
6-(1-isopropyl-piperidin-4-yloxy)-naphthalene-2-carboxylic acid benzyl-methyl-amide,
[6-(1-isopropyl-piperidin-4-yloxy)-naphthalen-2-yl]-thiomorpholin-4-yl-methanone,
6-(1-isopropyl-piperidin-4-yloxy)-naphthalene-2-carboxylic acid 3-methoxy-benzylamide,
[6-(1-isopropyl-piperidin-4-yloxy)-naphthalen-2-yl]-morpholin-4-yl-methanone,
(4-isopropyl-piperazin-1-yl)-[6-(1-isopropyl-pyrrolidin-3-yloxy)-naphthalen-2-yl]-methanone,
[6-(1-isobutyl-piperidin-4-yloxy)-naphthalen-2-yl]-(4-isopropyl-piperazin-1-yl)-methanone,
[6-(1-isopropyl-piperidin-4-yloxy)-naphthalen-2-yl]-piperidin-1-yl-methanone,
6-(3-piperidin-1-yl-propoxy)-naphthalene-2-carboxylic acid methyl-phenethyl-amide 1:1 hydrochloride,
6-(3-piperidin-1-yl-propoxy)-naphthalene-2-carboxylic acid benzyl-isopropyl-amide 1:1 hydrochloride,
azepan-1-yl-[6-(3-piperidin-1-yl-propoxy)-naphthalen-2-yl]-methanone 1:1 hydrochloride,
6-(3-piperidin-1-yl-propoxy)-naphthalene-2-carboxylic acid ethyl-(2-fluoro-benzyl)-amide 1:1 hydrochloride,
6-(3-piperidin-1-yl-propoxy)-naphthalene-2-carboxylic acid (2-dimethylamino-ethyl)-ethyl-amide 1:2 hydrochloride,
(4-benzyl-piperidin-1-yl)-[6-(3-piperidin-1-yl-propoxy)-naphthalen-2-yl]-methanone 1:1 hydrochloride,
(2-isopropyl-pyrrolidin-1-yl)-[6-(3-piperidin-1-yl-propoxy)-naphthalen-2-yl]-methanone 1:1 hydrochloride,
6-(1-isopropyl-piperidin-4-yloxy)-naphthalene-2-carboxylic acid methyl-(1-methyl-pyrrolidin-3-yl)-amide 1:2 hydrochloride,
[6-(1-isopropyl-piperidin-4-yloxy)-naphthalen-2-yl]-[4-(4-trifluoromethyl-phenyl)-piperazin-1-yl]-methanone 1:1 hydrochloride,
[6-(1-cyclopropyl-piperidin-4-yloxy)-naphthalen-2-yl]-morpholin-4-yl-methanone,
and pharmaceutically acceptable salts thereof.

Especially preferred are the following compounds of formula I of the present invention:
(4-methyl-piperidin-1-yl)-[6-(3-piperidin-1-yl-propoxy)-naphthalen-2-yl]-methanone,
(4-isopropyl-piperazin-1-yl)-[6-(3-piperidin-1-yl-propoxy)-naphthalen-2-yl]-methanone, (3,4-dihydro-1H-isoquinolin-2-yl)-[6-(3-piperidin-1-yl-propoxy)-naphthalen-2-yl]-methanone,

[6-(3-piperidin-1-yl-propoxy)-naphthalen-2-yl]-pyrrolidin-1-yl-methanone,

{6-[3-(2-methyl-piperidin-1-yl)-propoxy]-naphthalen-2-yl}-pyrrolidin-1-yl-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the formula II

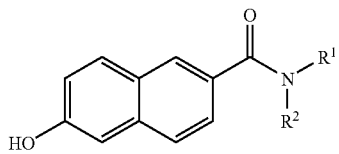

wherein $R^1$ and $R^2$ are as defined herein before,
with an alcohol of the formula III

HO-A          III wherein A is as defined herein before, in the presence of a trialkylphosphine or triphenylphosphine and of a diazo compound to obtain a compound of the formula I

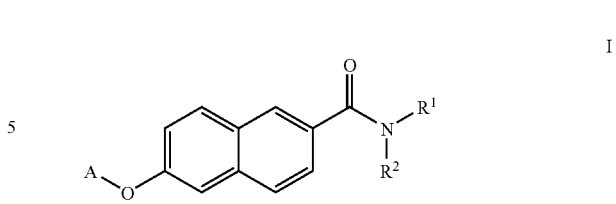

and if desired,
converting the compound obtained into a pharmaceutically acceptable acid addition salt, or, alternatively,
coupling the compound of formula VII

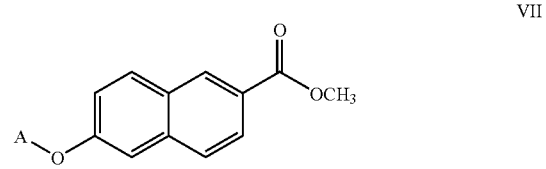

wherein A is as defined herein before,
with an amine of the formula V

H—NR¹R²          V wherein $R^1$ and $R^2$ are as defined herein before,
under basic conditions to obtain a compound of the formula I

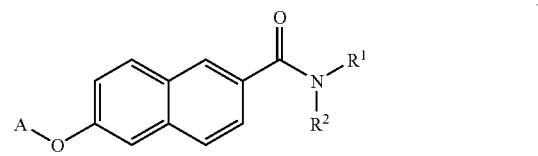

and if desired, converting the compound obtained into a pharmaceutically acceptable acid addition salt.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The preparation of compounds of formula I of the present invention may be carried out in sequential or convergent synthetic routes. Syntheses of the invention are shown in the following scheme. The skills required for carrying out the reaction and purification of the resulting products are known to those in the art. The substituents and indices used in the following description of the processes have the significance given above unless indicated to the contrary.

Scheme 1

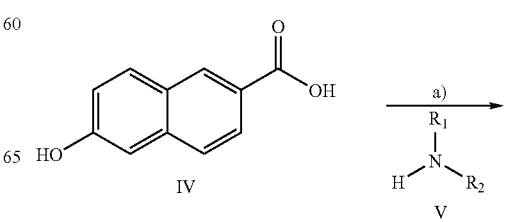

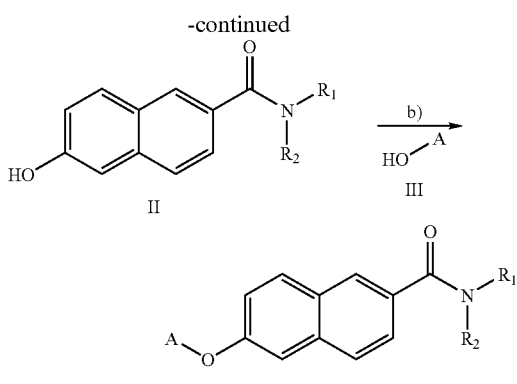

Compounds of general formula I can be prepared according to scheme 1 as follows: The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). 6-Hydroxy-2-naphtoic acid IV can conveniently be transformed to the respective amide through coupling with an amine V (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide derivatives II.

The syntheses of ethers are widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The transformation can be affected by employing reaction conditions which are commonly utilised in the so called "Mitsunobu reaction" which is known to those in the art and widely described (Hughes, David L. The Mitsunobu reaction. Organic Reactions (New York) (1992), 42, 335-656.) We find it convenient to couple amide II with alcohols III (either commercially available or accessible by methods described in references or by methods known in the art; as appropriate) under conditions employing a phosphine like a trialkylphosphine such as tributylphosphine ((n-Bu)$_3$P), triphenylphosphine (Ph$_3$P) and the like and a diazo-compound like diethyl-azodicarboxylate (DEAD), diisopropyl-azodicarboxylate (DIAD) (optionally polymer bound), tetramethyl azodicarboxamide and the like in a solvent commonly used in such transformations like tetrahydrofurane (THF), toluene, dichloromethane and the like. There is no particular restriction on the nature of the solvent to be employed, provided that it has no adverse effect on the reaction or the reagents involved and that it can dissolve the reagents, at least to some extent. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the title compounds I.

Alternatively, the sequence of recation steps can be reversed according to scheme 2. First alcohol III is reacted with ester VI under Mitsunobu reaction conditions followed by cleavage of the ester. The intermediately formed acid is then coupled with amine IV to arrive at compound I. Suitable coupling agents and conditions are described under step a) above.

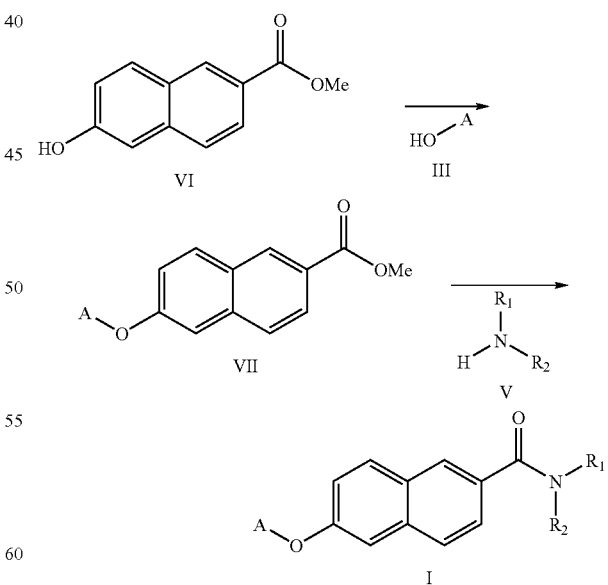

As described above,

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Intermediate A (6-Hydroxy-naphthalen-2-yl)-piperidin-1-yl-methanone

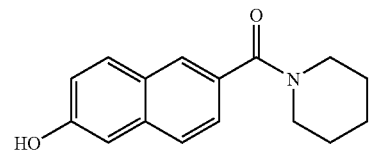

A mixture of 0.5 g (0.003 mol) 6-hydroxy-2-naphtoic acid, 1.2 g (0.003 mol) 2-(1H-benzotriazol-1-yl)-1,1,3,3-tetramethyluronium tetrafluoroborate, 2.3 ml (0.013 mol) N-ethyldiisopropylamine and 0.29 ml (0.030 mol) piperidine in 10 ml DMF was stirred for 16 h at room temperature. The mixture was concentrated to dryness and 50 ml ethyl acetate, 30 ml water and 20 ml NaHCO$_3$ aq. (10%) was added. The aqueous phase was extracted with 50 ml ethyl acetate and the combined organic layers were purified with column chromatography on silica. The product fractions were concentrated to dryness and titurated twice with 20 ml diethyl ether/heptane 1/1. The residue was dried under vacuum at 50° C. to yield 0.58 g (0.0227 mmol; 85%) of the title compound as light brown solid. MS (m/e): 254.3 (MH$^-$, 100%)

Intermediate B (6-Hydroxy-naphthalen-2-yl)-(4-methyl-piperidin-1-yl)-methanone

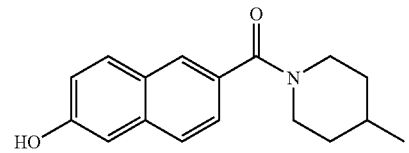

The title compound was synthesised from 6-hydroxy-2-naphtoic acid (commercially available) and 4-methyl-piperidine (commercially available) according to the procedure described for Example A. MS (m/e): 268.5 (MH$^-$, 100%)

Intermediate C (6-Hydroxy-naphthalen-2-yl)-(4-isopropyl-piperazin-1-yl)-methanone

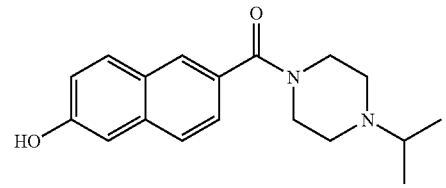

The title compound was synthesised from 6-hydroxy-2-naphtoic acid (commercially available) and N-isopropylpiperazine (commercially available) according to the procedure described for Example A. MS (m/e): 299.3 (MH⁺, 100%)

Intermediate D (6-Hydroxy-naphthalen-2-yl)-(2-methyl-pyrrolidin-1-yl)-methanone

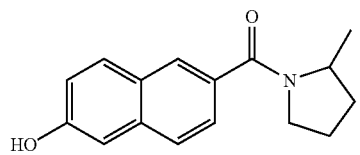

The title compound was synthesised from 6-Hydroxy-2-naphtoic acid (commercially available) and 2-methyl-pyrrolidine (commercially available) according to the procedure described for Example A. MS (m/e): 254.1 (MH⁻, 100%)

Intermediate E (3,4-Dihydro-1H-isoquinolin-2-yl)-(6-hydroxy-naphthalen-2-yl)-methanone

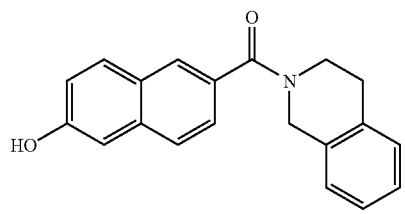

The title compound was synthesised from 6-hydroxy-2-naphtoic acid (commercially available) and 1,2,3,4-tetrahydroisochinoline (commercially available) according to the procedure described for Example A. MS (m/e): 302.1 (MH⁻, 100%)

Intermediate F

6-Hydroxy-naphthalene-2-carboxylic acid benzyl-methyl-amide

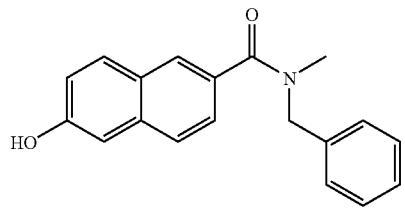

The title compound was synthesised from 6-hydroxy-2-naphtoic acid (commercially available) and N-methylbenzylamine (commercially available) according to the procedure described for Example A. MS (m/e): 290.1 (MH⁻, 100%)

Intermediate G (6-Hydroxy-naphthalen-2-yl)-thiomorpholin-4-yl-methanone

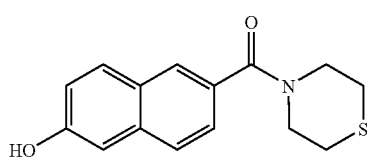

The title compound was synthesised from 6-hydroxy-2-naphtoic acid (commercially available) and thiomorpholine (commercially available) according to the procedure described for Example A. MS (m/e): 272.0 (MH⁻, 100%)

Intermediate H (6-Hydroxy-naphthalen-2-yl)-(4-methoxy-piperidin-1-yl)-methanone

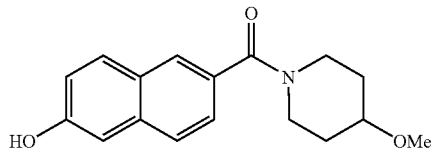

The title compound was synthesised from 6-hydroxy-2-naphtoic acid (commercially available) and 4-methoxy-piperidine (commercially available) according to the procedure described for Example A. MS (m/e): 284.0 (MH⁻, 100%)

Intermediate I

6-Hydroxy-naphthalene-2-carboxylic acid 3-methoxy-benzylamide

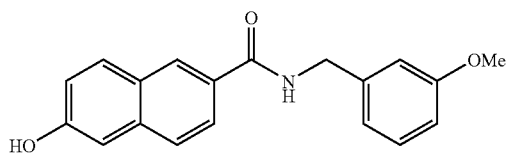

The title compound was synthesised from 6-hydroxy-2-naphtoic acid (commercially available) and 3-methoxy-benzylamine (commercially available) according to the procedure described for Example A. MS (m/e): 306.2 (MH⁻, 100%)

Intermediate J (6-Hydroxy-naphthalen-2-yl)-morpholin-4-yl-methanone

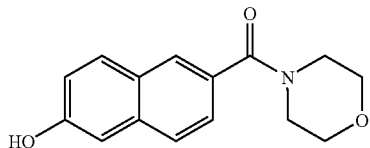

The title compound was synthesised from 6-hydroxy-2-naphtoic acid (commercially available) and morpholine (commercially available) according to the procedure described for Example A. MS (m/e): 256.0 (MH$^-$, 100%)

Intermediate K (6-Hydroxy-naphthalen-2-yl)-pyrrolidin-1-yl-methanone

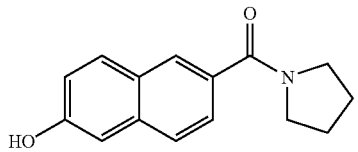

The title compound was synthesised from 6-hydroxy-2-naphtoic acid (commercially available) and pyrrolidine (commercially available) according to the procedure described for Example A. MS (m/e): 240.4 (MH$^-$, 100%)

Intermediate L 6-(3-Piperidin-1-yl-propoxy)-naphthalene-2-carboxylic acid methyl ester

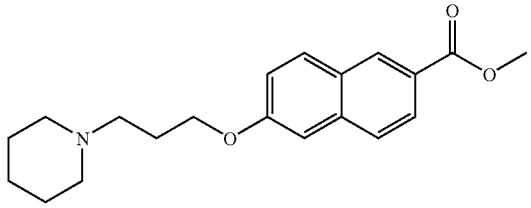

A mixture of 20.2 g (0.1 mol) 6-hydroxy-naphthalene-2-carboxylic acid methyl ester (commercially available), 18.6 g (0.13 mol) 1-piperidinepropanol (commercially available), 50.4 g (0.2 mol) 1,1'-(azodicarbonyl)dipiperidine and 58 ml (0.2 mol) tri-n-butyl-phosphine in 400 ml THF was stirred at room temperature for 16 h. The suspension was filtered off and the filtrate evaoprated to dryness. The residue was taken up in 200 ml DCM and 400 g Isolute® HM-N (Argonaut Technologies Inc., support material for accelerated solvent extraction) was added and evaporated to dryness. The residue was chromatographed over silica eluting with a gradient formed from DCM/MeOH(2N NH3) 99/1 to 9/1. After evaporation the residue was treated with heptan/diethyl ether and the precipitate filtered of and washed again with heptan/ diethyl ether. After drying under reduced pressure at 50° C. 25 g (76%) of the title compound was obtained as white solid. MS (m/e): 328.3 (MH$^+$, 100%)

Intermediate M 6-(3-Piperidin-1-yl-propoxy)-naphthalene-2-carboxylic acid 1:1 hydrochloride

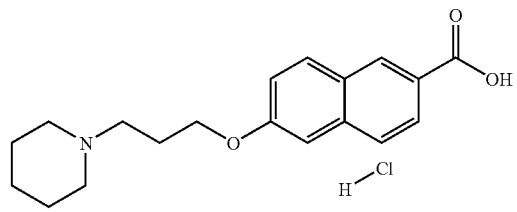

A mixture of 24.1 g (0.074 mol) 6-(3-piperidin-1-yl-propoxy)-naphthalene-2-carboxylic acid methyl ester (intermediate L) and 3.4 g (0.081 mol) LiOH H$_2$O in 250 ml THF, 100 ml water and 50 ml methanol was heated to reflux for 1 h. After evaporation of the organic solvents 200 ml ice/water was added and 50 ml 4 N HCl was added. The precipitate was filtered off washed with water, acetonitrile and diethylether and dryed under reduced pressure at 80° C. to yield 22.6 g (88%) of the title compound as white solid. MS (m/e): 314.0 (MH$^+$, 100%)

Intermediate N 6-(1-Isopropyl-piperidin-4-yloxy)-naphthalene-2-carboxylic acid methyl ester

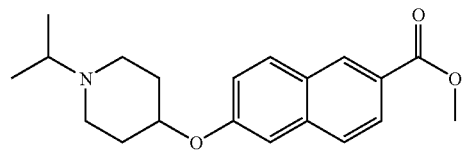

According to the procedure described for the synthesis of 6-(3-piperidin-1-yl-propoxy)-naphthalene-2-carboxylic acid methyl ester (intermediate L) the title compound was synthesised from 6-(3-piperidin-1-yl-propoxy)-naphthalene-2-carboxylic acid methyl ester (commercially available) and 1-isopropyl-piperidin-4-ol (prepared according to Acta Physica et Chemica 1980, 26(3-4), 177-184). MS (m/e): 328.3 (MH$^+$, 100%)

Intermediate O 6-(1-Isopropyl-piperidin-4-yloxy)-naphthalene-2-carboxylic acid 1:1 hydrochloride

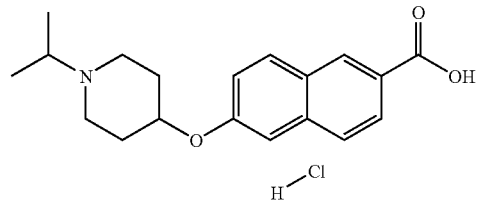

According to the procedure described for the synthesis of 6-(3-piperidin-1-yl-propoxy)-naphthalene-2-carboxylic acid 1:1 hydrochloride (intermediate M) the title compound was synthesised from 6-(1-isopropyl-piperidin-4-yloxy)-naphthalene-2-carboxylic acid methyl ester (intermediate N) and LiOH. MS (m/e): 314.0 (MH$^+$, 100%)

Example 1

Piperidin-1-yl-[6-(3-piperidin-1-yl-propoxy)-naphthalen-2-yl]-methanone 1:1 hydrochloride A mixture of 51 mg (0.2 mmol) (6-hydroxy-naphthalen-2-yl)-piperidin-1-yl-methanone, 350 mg (ca. 3 mmol) polymerbound triphenylphospine (Fluka), 34 mg (0.24 mmol) piperidinepropanol and 92 mg (0.4 mmol) di-tert.-butyl azadicarboxylate in 2 ml THF was stirred for a prolonged period of time at room temperature. The mixture was filtered through a pad of silica and washed with 3 ml THF. HCl in methanol was added (0.8 ml; 1.25 M) and the mixture was evaporated to dryness. The residue was taken up in methanol and purified with preparative HPLC on reversed phase eluting with acetonitrile/water/HCl. The combined product fractions were evaporated under reduced pressure to yield 40 mg (46%) of the title compound as light brown foam. MS (m/e): 381.3 (MH$^+$, 100%)

According to the procedure described for the synthesis of Example 1 further derivatives have been synthesised from the respective (6-Hydroxy-naphthalen-2-yl)-amine-4-yl-methanone and the respective alcohol. The results are shown in Table 1 and comprise Example 1 to Example 73:

TABLE 1

| Ex. No | Systematic name | MW | Starting materials | MW found (M + H)$^+$ |
|---|---|---|---|---|
| 1 | piperidin-1-yl-[6-(3-piperidin-1-yl-propoxy)-naphthalen-2-yl]-methanone 1:1 hydrochloride | 380.5 | (6-hydroxy-naphthalen-2-yl)-piperidin-1-yl-methanone (Intermediate A) and 3-piperidin-1-yl-propan-1-ol (commercially available) | 381.3 |
| 2 | (4-methyl-piperidin-1-yl)-[6-(3-piperidin-1-yl-propoxy)-naphthalen-2-yl]-methanone 1:1 hydrochloride | 394.6 | (6-hydroxy-naphthalen-2-yl)-(4-methyl-piperidin-1-yl)-methanone (Intermediate B) and 3-piperidin-1-yl-propan-1-ol (commercially available) | 395.4 |
| 3 | (4-methyl-piperidin-1-yl)-{6-[3-(2-methyl-piperidin-1-yl)-propoxy]-naphthalen-2-yl}-methanone 1:1 hydrochloride | 408.6 | (6-hydroxy-naphthalen-2-yl)-(4-methyl-piperidin-1-yl)-methanone (Intermediate B) and 3-(2-methyl-piperidin-1-yl)-propan-1-ol (commercially available) | 409.3 |
| 4 | (4-isopropyl-piperazin-1-yl)-[6-(3-piperidin-1-yl-propoxy)-naphthalen-2-yl]-methanone 1:2 hydrochloride | 423.6 | (6-hydroxy-naphthalen-2-yl)-(4-isopropyl-piperazin-1-yl)-methanone (Intermediate C) and 3-piperidin-1-yl-propan-1-ol (commercially available) | 424.1 |
| 5 | (4-isopropyl-piperazin-1-yl)-{6-[2-(1-methyl-piperidin-2-yl)-ethoxy]-naphthalen-2-yl}-methanone 1:2 hydrochloride | 423.6 | (6-hydroxy-naphthalen-2-yl)-(4-isopropyl-piperazin-1-yl)-methanone (Intermediate C) and 2-(1-methyl-piperidin-2-yl)-ethanol (commercially available) | 424.3 |
| 6 | (2-methyl-pyrrolidin-1-yl)-[6-(3-piperidin-1-yl-propoxy)-naphthalen-2-yl]-methanone 1:1 hydrochloride | 380.5 | (6-hydroxy-naphthalen-2-yl)-(2-methyl-pyrrolidin-1-yl)-methanone (Intermediate D) and 3-piperidin-1-yl-propan-1-ol (commercially available) | 381.1 |
| 7 | {6-[3-(2-methyl-piperidin-1-yl)-propoxy]-naphthalen-2-yl}-(2-methyl-pyrrolidin-1-yl)-methanone 1:1 hydrochloride | 394.6 | (6-hydroxy-naphthalen-2-yl)-(2-methyl-pyrrolidin-1-yl)-methanone (Intermediate D) and 3-(2-methyl-piperidin-1-yl)-propan-1-ol (commercially available) | 395.3 |
| 8 | {6-[2-(1-methyl-piperidin-2-yl)-ethoxy]-naphthalen-2-yl}-(2-methyl-pyrrolidin-1-yl)-methanone 1:1 hydrochloride | 380.5 | (6-hydroxy-naphthalen-2-yl)-(2-methyl-pyrrolidin-1-yl)-methanone (Intermediate D) and 2-(1-methyl-piperidin-2-yl)-ethanol (commercially available) | 381.3 |
| 9 | (3,4-dihydro-1H-isoquinolin-2-yl)-[6-(3-piperidin-1-yl-propoxy)-naphthalen-2-yl]-methanone 1:1 hydrochloride | 428.6 | (3,4-dihydro-1H-isoquinolin-2-yl)-(6-hydroxy-naphthalen-2-yl)-methanone (Intermediate E) and 3-piperidin-1-yl-propan-1-ol (commercially available) | 429.5 |
| 10 | (3,4-dihydro-1H-isoquinolin-2-yl)-{6-[3-(2-methyl-piperidin-1-yl)-propoxy]-naphthalen-2-yl}-methanone 1:1 hydrochloride | 442.6 | (3,4-dihydro-1H-isoquinolin-2-yl)-(6-hydroxy-naphthalen-2-yl)-methanone (Intermediate E) and 3-(2-methyl-piperidin-1-yl)-propan-1-ol (commercially available) | 443.3 |

TABLE 1-continued

| Ex. No | Systematic name | MW | Starting materials | MW found (M + H)+ |
|---|---|---|---|---|
| 11 | (3,4-dihydro-1H-isoquinolin-2-yl)-{6-[2-(1-methyl-piperidin-2-yl)-ethoxy]-naphthalen-2-yl}-methanone 1:1 hydrochloride | 428.6 | (3,4-dihydro-1H-isoquinolin-2-yl)-(6-hydroxy-naphthalen-2-yl)-methanone (Intermediate E) and 2-(1-methyl-piperidin-2-yl)-ethanol (commercially available) | 429.5 |
| 12 | 6-(3-piperidin-1-yl-propoxy)-naphthalene-2-carboxylic acid benzyl-methyl-amide 1:1 hydrochloride | 416.6 | 6-hydroxy-naphthalene-2-carboxylic acid benzyl-methyl-amide (Intermediate F) and 3-piperidin-1-yl-propan-1-ol (commercially available) | 417.3 |
| 13 | 6-[3-(2-methyl-piperidin-1-yl)-propoxy]-naphthalene-2-carboxylic acid benzyl-methyl-amide 1:1 hydrochloride | 430.6 | 6-hydroxy-naphthalene-2-carboxylic acid benzyl-methyl-amide (Intermediate F) and 3-(2-methyl-piperidin-1-yl)-propan-1-ol (commercially available) | 431.4 |
| 14 | [6-(3-piperidin-1-yl-propoxy)-naphthalen-2-yl]-thiomorpholin-4-yl-methanone 1:1 hydrochloride | 398.6 | (6-hydroxy-naphthalen-2-yl)-thiomorpholin-4-yl-methanone (Intermediate G) and 3-piperidin-1-yl-propan-1-ol (commercially available) | 399.4 |
| 15 | [6-(3-morpholin-4-yl-propoxy)-naphthalen-2-yl]-thiomorpholin-4-yl-methanone 1:1 hydrochloride | 400.5 | (6-hydroxy-naphthalen-2-yl)-thiomorpholin-4-yl-methanone (Intermediate G) and 3-morpholin-4-yl-propan-1-ol (commercially available) | 401.5 |
| 16 | {6-[3-(2-methyl-piperidin-1-yl)-propoxy]-naphthalen-2-yl}-thiomorpholin-4-yl-methanone 1:1 hydrochloride | 412.6 | (6-hydroxy-naphthalen-2-yl)-thiomorpholin-4-yl-methanone (Intermediate G) and 3-(2-methyl-piperidin-1-yl)-propan-1-ol (commercially available) | 413.4 |
| 17 | {6-[2-(1-methyl-piperidin-2-yl)-ethoxy]-naphthalen-2-yl}-thiomorpholin-4-yl-methanone hydrochloride | 398.6 | (6-hydroxy-naphthalen-2-yl)-thiomorpholin-4-yl-methanone (Intermediate G) and 2-(1-methyl-piperidin-2-yl)-ethanol (commercially available) | 399.4 |
| 18 | (4-methoxy-piperidin-1-yl)-[6-(3-piperidin-1-yl-propoxy)-naphthalen-2-yl]-methanone 1:1 hydrochloride | 410.6 | (6-hydroxy-naphthalen-2-yl)-(4-methoxy-piperidin-1-yl)-methanone (Intermediate H) and 3-piperidin-1-yl-propan-1-ol (commercially available) | 411.3 |
| 19 | (4-methoxy-piperidin-1-yl)-{6-[3-(2-methyl-piperidin-1-yl)-propoxy]-naphthalen-2-yl}-methanone 1:1 hydrochloride | 424.6 | (6-hydroxy-naphthalen-2-yl)-(4-methoxy-piperidin-1-yl)-methanone (Intermediate H) and 3-(2-methyl-piperidin-1-yl)-propan-1-ol (commercially available) | 425.4 |
| 20 | (4-methoxy-piperidin-1-yl)-{6-[2-(1-methyl-piperidin-2-yl)-ethoxy]-naphthalen-2-yl}-methanone 1:1 hydrochloride | 410.6 | (6-hydroxy-naphthalen-2-yl)-(4-methoxy-piperidin-1-yl)-methanone (Intermediate H) and 2-(1-methyl-piperidin-2-yl)-ethanol (commercially available) | 411.3 |
| 21 | 6-(3-piperidin-1-yl-propoxy)-naphthalene-2-carboxylic acid 3-methoxy-benzylamide 1:1 hydrochloride | 432.6 | 6-hydroxy-naphthalene-2-carboxylic acid 3-methoxy-benzylamide (Intermediate I) and 3-piperidin-1-yl-propan-1-ol (commercially available) | 433.4 |
| 22 | 6-[3-(2-methyl-piperidin-1-yl)-propoxy]-naphthalene-2-carboxylic acid 3-methoxy-benzylamide 1:1 hydrochloride | 446.6 | 6-hydroxy-naphthalene-2-carboxylic acid 3-methoxy-benzylamide (Intermediate I) and 3-(2-methyl-piperidin-1-yl)-propan-1-ol (commercially available) | 447.4 |
| 23 | morpholin-4-yl-[6-(3-morpholin-4-yl-propoxy)-naphthalen-2-yl]-methanone 1:1 hydrochloride | 384.5 | (6-hydroxy-naphthalen-2-yl)-morpholin-4-yl-methanone (Intermediate J) and 3-morpholin-4-yl-propan-1-ol (commercially available) | 385.5 |
| 24 | {6-[3-(2-methyl-piperidin-1-yl)-propoxy]-naphthalen-2-yl}-morpholin-4-yl-methanone 1:1 hydrochloride | 396.5 | (6-hydroxy-naphthalen-2-yl)-morpholin-4-yl-methanone (Intermediate J) and 3-(2-methyl-piperidin-1-yl)-propan-1-ol (commercially available) | 397.4 |

TABLE 1-continued

| Ex. No | Systematic name | MW | Starting materials | MW found (M + H)+ |
|---|---|---|---|---|
| 25 | {6-[2-(1-methyl-piperidin-2-yl)-ethoxy]-naphthalen-2-yl}-morpholin-4-yl-methanone 1:1 hydrochloride | 382.5 | (6-hydroxy-naphthalen-2-yl)-morpholin-4-yl-methanone (Intermediate J) and 2-(1-methyl-piperidin-2-yl)-ethanol (commercially available) | 383.4 |
| 26 | [6-(3-piperidin-1-yl-propoxy)-naphthalen-2-yl]-pyrrolidin-1-yl-methanone 1:1 hydrochloride | 366.5 | (6-hydroxy-naphthalen-2-yl)-pyrrolidin-1-yl-methanone (Intermediate K) and 3-piperidin-1-yl-propan-1-ol (commercially available) | 367.3 |
| 27 | {6-[3-(2-methyl-piperidin-1-yl)-propoxy]-naphthalen-2-yl}-pyrrolidin-1-yl-methanone 1:1 hydrochloride | 380.5 | (6-hydroxy-naphthalen-2-yl)-pyrrolidin-1-yl-methanone (Intermediate K) and 3-(2-methyl-piperidin-1-yl)-propan-1-ol (commercially available) | 381.4 |
| 28 | {6-[2-(1-methyl-pyrrolidin-2-yl)-ethoxy]-naphthalen-2-yl}-piperidin-1-yl-methanone 1:1 hydrochloride | 366.5 | (6-hydroxy-naphthalen-2-yl)-piperidin-1-yl-methanone (Intermediate A) and 2-(1-methyl-pyrrolidin-2-yl)-ethanol (commercially available) | 367.4 |
| 29 | [6-(1-isopropyl-pyrrolidin-3-yloxy)-naphthalen-2-yl]-piperidin-1-yl-methanone 1:1 hydrochloride | 366.5 | (6-hydroxy-naphthalen-2-yl)-piperidin-1-yl-methanone (Intermediate A) and 1-isopropyl-pyrrolidin-3-ol (commercially available) | 367.5 |
| 30 | [6-(1-isobutyl-piperidin-4-yloxy)-naphthalen-2-yl]-piperidin-1-yl-methanone 1:1 hydrochloride | 394.6 | (6-hydroxy-naphthalen-2-yl)-piperidin-1-yl-methanone (Intermediate A) and 1-isobutyl-piperidin-4-ol (commercially available) | 395.4 |
| 31 | (4-methyl-piperidin-1-yl)-{6-[2-(1-methyl-pyrrolidin-2-yl)-ethoxy]-naphthalen-2-yl}-methanone 1:1 hydrochloride | 380.5 | (6-hydroxy-naphthalen-2-yl)-(4-methyl-piperidin-1-yl)-methanone (Intermediate B) and 2-(1-methyl-pyrrolidin-2-yl)-ethanol (commercially available) | 381.3 |
| 32 | [6-(1-isopropyl-pyrrolidin-3-yloxy)-naphthalen-2-yl]-(4-methyl-piperidin-1-yl)-methanone 1:1 hydrochloride | 380.5 | (6-hydroxy-naphthalen-2-yl)-(4-methyl-piperidin-1-yl)-methanone (Intermediate B) and 1-isopropyl-pyrrolidin-3-ol (commercially available) | 381.3 |
| 33 | [6-(1-isopropyl-piperidin-4-yloxy)-naphthalen-2-yl]-(4-methyl-piperidin-1-yl)-methanone 1:1 hydrochloride | 394.6 | (6-hydroxy-naphthalen-2-yl)-(4-methyl-piperidin-1-yl)-methanone (Intermediate B) and 1-isopropyl-piperidin-4-ol (Acta Physica et Chemica 1980, 26(3–4), 177–184) | 395.4 |
| 34 | [6-(1-isobutyl-piperidin-4-yloxy)-naphthalen-2-yl]-(4-methyl-piperidin-1-yl)-methanone 1:1 hydrochloride | 408.6 | (6-hydroxy-naphthalen-2-yl)-(4-methyl-piperidin-1-yl)-methanone (Intermediate B) and 1-isobutyl-piperidin-4-ol (commercially available) | 409.5 |
| 35 | (2-methyl-pyrrolidin-1-yl)-{6-[2-(1-methyl-pyrrolidin-2-yl)-ethoxy]-naphthalen-2-yl}-methanone 1:1 hydrochloride | 366.5 | (6-hydroxy-naphthalen-2-yl)-(4-methyl-piperidin-1-yl)-methanone (Intermediate B) and 1-isopropyl-piperidin-4-ol (Acta Physica et Chemica 1980, 26(3–4), 177–184) | 367.3 |
| 36 | [6-(1-isopropyl-pyrrolidin-3-yloxy)-naphthalen-2-yl]-(2-methyl-pyrrolidin-1-yl)-methanone 1:1 hydrochloride | 366.5 | (6-hydroxy-naphthalen-2-yl)-(2-methyl-pyrrolidin-1-yl)-methanone and 1-isopropyl-pyrrolidin-3-ol (commercially available) | 367.3 |
| 37 | [6-(1-isopropyl-piperidin-4-yloxy)-naphthalen-2-yl]-(2-methyl-pyrrolidin-1-yl)-methanone 1:1 hydrochloride | 380.5 | (6-hydroxy-naphthalen-2-yl)-(2-methyl-pyrrolidin-1-yl)-methanone (Intermediate D) and 1-isopropyl-piperidin-4-ol (Acta Physica et Chemica 1980, 26(3–4), 177–184) | 381.3 |
| 38 | [6-(1-isobutyl-piperidin-4-yloxy)-naphthalen-2-yl]-(2-methyl-pyrrolidin-1-yl)-methanone 1:1 hydrochloride | 394.6 | (6-hydroxy-naphthalen-2-yl)-(2-methyl-pyrrolidin-1-yl)-methanone (Intermediate D) and 1-isobutyl-piperidin-4-ol (commercially available) | 395.4 |

TABLE 1-continued

| Ex. No | Systematic name | MW | Starting materials | MW found (M + H)+ |
|---|---|---|---|---|
| 39 | (3,4-dihydro-1H-isoquinolin-2-yl)-{6-[2-(1-methyl-pyrrolidin-2-yl)-ethoxy]-naphthalen-2-yl}-methanone 1:1 hydrochloride | 414.5 | (3,4-dihydro-1H-isoquinolin-2-yl)-(6-hydroxy-naphthalen-2-yl)-methanone (Intermediate E) and 2-(1-methyl-pyrrolidin-2-yl)-ethanol (commercially available) | 415.4 |
| 40 | (3,4-dihydro-1H-isoquinolin-2-yl)-[6-(1-isopropyl-pyrrolidin-3-yloxy)-naphthalen-2-yl]-methanone 1:1 hydrochloride | 414.5 | (3,4-dihydro-1H-isoquinolin-2-yl)-(6-hydroxy-naphthalen-2-yl)-methanone (Intermediate E) and 1-isopropyl-pyrrolidin-3-ol (commercially available) | 415.4 |
| 41 | (3,4-dihydro-1H-isoquinolin-2-yl)-[6-(1-isopropyl-piperidin-4-yloxy)-naphthalen-2-yl]-methanone 1:1 hydrochloride | 428.6 | (3,4-dihydro-1H-isoquinolin-2-yl)-(6-hydroxy-naphthalen-2-yl)-methanone (Intermediate E) and 1-isopropyl-piperidin-4-ol (Acta Physica et Chemica 1980, 26(3–4), 177–184) | 429.6 |
| 42 | (3,4-dihydro-1H-isoquinolin-2-yl)-[6-(1-isobutyl-piperidin-4-yloxy)-naphthalen-2-yl]-methanone 1:1 hydrochloride | 442.6 | (3,4-dihydro-1H-isoquinolin-2-yl)-(6-hydroxy-naphthalen-2-yl)-methanone (Intermediate E) and 1-isobutyl-piperidin-4-ol (commercially available) | 443.4 |
| 43 | (3,4-dihydro-1H-isoquinolin-2-yl)-[6-(1-methyl-piperidin-3-ylmethoxy)-naphthalen-2-yl]-methanone 1:1 hydrochloride | 414.5 | (3,4-dihydro-1H-isoquinolin-2-yl)-(6-hydroxy-naphthalen-2-yl)-methanone (Intermediate E) and (1-methyl-piperidin-3-yl)-methanol (commercially available) | 415.5 |
| 44 | 6-[2-(1-methyl-pyrrolidin-2-yl)-ethoxy]-naphthalene-2-carboxylic acid benzyl-methyl-amide 1:1 hydrochloride | 402.5 | 6-hydroxy-naphthalene-2-carboxylic acid benzyl-methyl-amide (Intermediate F) and 2-(1-methyl-pyrrolidin-2-yl)-ethanol (commercially available) | 403.5 |
| 45 | 6-(1-isopropyl-pyrrolidin-3-yloxy)-naphthalene-2-carboxylic acid benzyl-methyl-amide 1:1 hydrochloride | 402.5 | 6-hydroxy-naphthalene-2-carboxylic acid benzyl-methyl-amide (Intermediate F) and 1-isopropyl-pyrrolidin-3-ol (commercially available) | 403.6 |
| 46 | 6-(1-isopropyl-piperidin-4-yloxy)-naphthalene-2-carboxylic acid benzyl-methyl-amide 1:1 hydrochloride | 416.6 | 6-hydroxy-naphthalene-2-carboxylic acid benzyl-methyl-amide (Intermediate F) and 1-isopropyl-piperidin-4-ol (Acta Physica et Chemica 1980, 26(3–4), 177–184) | 417.4 |
| 47 | 6-(1-isobutyl-piperidin-4-yloxy)-naphthalene-2-carboxylic acid benzyl-methyl-amide 1:1 hydrochloride | 430.6 | 6-hydroxy-naphthalene-2-carboxylic acid benzyl-methyl-amide (Intermediate F) and 1-isobutyl-piperidin-4-ol (commercially available) | 431.5 |
| 48 | {6-[2-(1-methyl-pyrrolidin-2-yl)-ethoxy]-naphthalen-2-yl}-thiomorpholin-4-yl-methanone 1:1 hydrochloride | 384.5 | (6-hydroxy-naphthalen-2-yl)-thiomorpholin-4-yl-methanone (Intermediate G) and 2-(1-methyl-pyrrolidin-2-yl)-ethanol (commercially available) | 385.5 |
| 49 | [6-(1-isopropyl-pyrrolidin-3-yloxy)-naphthalen-2-yl]-thiomorpholin-4-yl-methanone 1:1 hydrochloride | 384.5 | (6-hydroxy-naphthalen-2-yl)-thiomorpholin-4-yl-methanone (Intermediate G) and 1-isopropyl-pyrrolidin-3-ol (commercially available) | 385.4 |
| 50 | [6-(1-isopropyl-piperidin-4-yloxy)-naphthalen-2-yl]-thiomorpholin-4-yl-methanone 1:1 hydrochloride | 398.6 | (6-hydroxy-naphthalen-2-yl)-thiomorpholin-4-yl-methanone (Intermediate G) and 1-isopropyl-piperidin-4-ol (Acta Physica et Chemica 1980, 26(3–4), 177–184) | 399.5 |
| 51 | [6-(1-isobutyl-piperidin-4-yloxy)-naphthalen-2-yl]-thiomorpholin-4-yl-methanone 1:1 hydrochloride | 412.6 | (6-hydroxy-naphthalen-2-yl)-thiomorpholin-4-yl-methanone (Intermediate G) and 1-isobutyl-piperidin-4-ol (commercially available) | 413.5 |
| 52 | (4-methoxy-piperidin-1-yl)-{6-[2-(1-methyl-pyrrolidin-2-yl)-ethoxy]-naphthalen-2-yl}-methanone 1:1 hydrochloride | 396.5 | (6-hydroxy-naphthalen-2-yl)-(4-methoxy-piperidin-1-yl)-methanone (Intermediate H) and 2-(1-methyl-pyrrolidin-2-yl)-ethanol (commercially available) | 397.5 |

TABLE 1-continued

| Ex. No | Systematic name | MW | Starting materials | MW found (M + H)+ |
|---|---|---|---|---|
| 53 | [6-(1-isopropyl-pyrrolidin-3-yloxy)-naphthalen-2-yl]-(4-methoxy-piperidin-1-yl)-methanone 1:1 hydrochloride | 396.5 | (6-hydroxy-naphthalen-2-yl)-(4-methoxy-piperidin-1-yl)-methanone (Intermediate H) and 1-isopropyl-pyrrolidin-3-ol (commercially available) | 397.4 |
| 54 | [6-(1-isopropyl-piperidin-4-yloxy)-naphthalen-2-yl]-(4-methoxy-piperidin-1-yl)-methanone 1:1 hydrochloride | 410.6 | (6-hydroxy-naphthalen-2-yl)-(4-methoxy-piperidin-1-yl)-methanone (Intermediate H) and 1-isopropyl-piperidin-4-ol (Acta Physica et Chemica 1980, 26(3–4), 177–184) | 411.5 |
| 55 | [6-(1-isobutyl-piperidin-4-yloxy)-naphthalen-2-yl]-(4-methoxy-piperidin-1-yl)-methanone 1:1 hydrochloride | 424.6 | (6-hydroxy-naphthalen-2-yl)-(4-methoxy-piperidin-1-yl)-methanone (Intermediate H) and 1-isobutyl-piperidin-4-ol (commercially available) | 425.4 |
| 56 | 6-[2-(1-methyl-pyrrolidin-2-yl)-ethoxy]-naphthalene-2-carboxylic acid 3-methoxy-benzylamide 1:1 hydrochloride | 418.5 | 6-hydroxy-naphthalene-2-carboxylic acid 3-methoxy-benzylamide (Intermediate I) and 2-(1-methyl-pyrrolidin-2-yl)-ethanol (commercially available) | 419.4 |
| 57 | 6-(1-isopropyl-pyrrolidin-3-yloxy)-naphthalene-2-carboxylic acid 3-methoxy-benzylamide 1:1 hydrochloride | 418.5 | 6-hydroxy-naphthalene-2-carboxylic acid 3-methoxy-benzylamide (Intermediate I) and 2-(1-methyl-pyrrolidin-2-yl)-ethanol (commercially available) | 419.3 |
| 58 | 6-(1-isopropyl-piperidin-4-yloxy)-naphthalene-2-carboxylic acid 3-methoxy-benzylamide 1:1 hydrochloride | 432.6 | 6-hydroxy-naphthalene-2-carboxylic acid 3-methoxy-benzylamide (Intermediate I) and 1-isopropyl-piperidin-4-ol (Acta Physica et Chemica 1980, 26(3–4), 177–184) | 433.4 |
| 59 | 6-(1-isobutyl-piperidin-4-yloxy)-naphthalene-2-carboxylic acid 3-methoxy-benzylamide 1:1 hydrochloride | 446.6 | 6-hydroxy-naphthalene-2-carboxylic acid 3-methoxy-benzylamide (Intermediate I) and 1-isobutyl-piperidin-4-ol (commercially available) | 447.4 |
| 60 | 6-(1-methyl-piperidin-3-ylmethoxy)-naphthalene-2-carboxylic acid 3-methoxy-benzylamide 1:1 hydrochloride | 418.5 | 6-hydroxy-naphthalene-2-carboxylic acid 3-methoxy-benzylamide (Intermediate I) and (1-methyl-piperidin-3-yl)-methanol (commercially available) | 419.3 |
| 61 | {6-[2-(1-methyl-pyrrolidin-2-yl)-ethoxy]-naphthalen-2-yl}-morpholin-4-yl-methanone 1:1 hydrochloride | 368.5 | (6-hydroxy-naphthalen-2-yl)-morpholin-4-yl-methanone (Intermediate J) and 2-(1-methyl-pyrrolidin-2-yl)-ethanol (commercially available) | 369.3 |
| 62 | [6-(1-isopropyl-pyrrolidin-3-yloxy)-naphthalen-2-yl]-morpholin-4-yl-methanone 1:1 hydrochloride | 368.5 | (6-hydroxy-naphthalen-2-yl)-morpholin-4-yl-methanone (Intermediate J) and 1-isopropyl-pyrrolidin-3-ol (commercially available) | 369.3 |
| 63 | [6-(1-isopropyl-piperidin-4-yloxy)-naphthalen-2-yl]-morpholin-4-yl-methanone 1:1 hydrochloride | 382.5 | (6-hydroxy-naphthalen-2-yl)-morpholin-4-yl-methanone (Intermediate J) and 1-isopropyl-piperidin-4-ol (Acta Physica et Chemica 1980, 26(3–4), 177–184) | 383.3 |
| 64 | [6-(1-isobutyl-piperidin-4-yloxy)-naphthalen-2-yl]-morpholin-4-yl-methanone 1:1 hydrochloride | 396.5 | (6-hydroxy-naphthalen-2-yl)-morpholin-4-yl-methanone (Intermediate J) and 1-isobutyl-piperidin-4-ol (commercially available) | 397.4 |

TABLE 1-continued

| Ex. No | Systematic name | MW | Starting materials | MW found (M + H)+ |
|---|---|---|---|---|
| 65 | {6-[2-(1-methyl-pyrrolidin-2-yl)-ethoxy]-naphthalen-2-yl}-pyrrolidin-1-yl-methanone 1:1 hydrochloride | 352.5 | (6-hydroxy-naphthalen-2-yl)-pyrrolidin-1-yl-methanone (Intermediate J) and 2-(1-methyl-pyrrolidin-2-yl)-ethanol (commercially available) | 353.3 |
| 66 | [6-(1-isopropyl-pyrrolidin-3-yloxy)-naphthalen-2-yl]-pyrrolidin-1-yl-methanone 1:1 hydrochloride | 352.5 | (6-hydroxy-naphthalen-2-yl)-pyrrolidin-1-yl-methanone (Intermediate J) and 1-isopropyl-pyrrolidin-3-ol (commercially available) | 353.4 |
| 67 | [6-(1-isopropyl-piperidin-4-yloxy)-naphthalen-2-yl]-pyrrolidin-1-yl-methanone 1:1 hydrochloride | 366.5 | (6-hydroxy-naphthalen-2-yl)-pyrrolidin-1-yl-methanone (Intermediate J) and 1-isopropyl-piperidin-4-ol (commercially available) | 367.3 |
| 68 | [6-(1-isobutyl-piperidin-4-yloxy)-naphthalen-2-yl]-pyrrolidin-1-yl-methanone 1:1 hydrochloride | 380.5 | (6-hydroxy-naphthalen-2-yl)-pyrrolidin-1-yl-methanone (Intermediate J) and 1-isobutyl-piperidin-4-ol (commercially available) | 381.4 |
| 69 | (4-isopropyl-piperazin-1-yl)-{6-[2-(1-methyl-pyrrolidin-2-yl)-ethoxy]-naphthalen-2-yl}-methanone 1:1 hydrochloride | 409.6 | (6-hydroxy-naphthalen-2-yl)-(4-isopropyl-piperazin-1-yl)-methanone (Intermediate C) and 2-(1-methyl-pyrrolidin-2-yl)-ethanol (commercially available) | 410.3 |
| 70 | (4-isopropyl-piperazin-1-yl)-[6-(1-isopropyl-pyrrolidin-3-yloxy)-naphthalen-2-yl]-methanone 1:1 hydrochloride | 409.6 | (6-hydroxy-naphthalen-2-yl)-(4-isopropyl-piperazin-1-yl)-methanone (Intermediate C) and 1-isopropyl-pyrrolidin-3-ol (commercially available) | 410.3 |
| 71 | [6-(1-isobutyl-piperidin-4-yloxy)-naphthalen-2-yl]-(4-isopropyl-piperazin-1-yl)-methanone 1:1 hydrochloride | 437.6 | (6-hydroxy-naphthalen-2-yl)-(4-isopropyl-piperazin-1-yl)-methanone (Intermediate C) and 1-isobutyl-piperidin-4-ol (commercially available) | 438.4 |
| 72 | (4-isopropyl-piperazin-1-yl)-[6-(1-methyl-piperidin-3-ylmethoxy)-naphthalen-2-yl]-methanone 1:1 hydrochloride | 409.6 | (6-hydroxy-naphthalen-2-yl)-(4-isopropyl-piperazin-1-yl)-methanone (Intermediate C) and (1-methyl-piperidin-3-yl)-methanol (commercially available) | 410.3 |
| 73 | [6-(1-isopropyl-piperidin-4-yloxy)-naphthalen-2-yl]-piperidin-1-yl-methanone 1:1 hydrochloride | 380.5 | (6-hydroxy-naphthalen-2-yl)-piperidin-1-yl-methanone (Intermediate A) and 1-isopropyl-piperidin-4-ol (Acta Physica et Chemica 1980, 26(3–4), 177–184) | 381.1 |

Example 74

(1,1-Dioxo-6-thiomorpholin-4-yl)-[6-(1-isopropyl-piperidin-4-yloxy)-naphthalen-2-yl]-methanone 1:1 hydrochloride A mixture of 0.12 g (0.3 mmol) [6-(1-Isopropyl-piperidin-4-yloxy)-naphthalen-2-yl]-thiomorpholin-4-yl-methanone 1:1 hydrochloride (Example 50) and 0.463 g (0.75 mmol) potassium monopersulfate triple salt (oxone®) in 5 ml methanol was stirred for 4 h at room temperature and filtered. The filtrate was evaporated to dryness and the residue was purified on silica eluting with DCM/2N $NH_3$ in MeOH 92/2 to 9/1. The product fractions were evaporated and the residue taken up in methanol and subsequently treated with 0.5 ml 1.25N HCl in methanol and evaporated to dryness to yield 16 mg (11%) of the title compound as slightly yellow foam. MS (m/e): 431.4 (MH+, 100%).

Example 75

[6-(2,2-Dimethyl-3-piperidin-1-yl-propoxy)-naphthalen-2-yl]-(4-methyl-piperidin-1-yl)-methanone The title compound was synthesised from (6-hydroxy-naphthalen-2-yl)-(4-methyl-piperidin-1-yl)-methanone (intermediate B) and 2,2-dimethyl-3-piperidin-1-yl-propan-1-ol (commercially available) according to the procedure described for the synthesis of Example 1.

MS (m/e): 423.1 (MH+, 100%)

According to the procedure described for the synthesis of Intermediate A further amide derivatives were synthesised from 6-(1-isopropyl-piperidin-4-yloxy)-naphthalene-2-carboxylic acid 1:1 hydrochloride or 6-(3-piperidin-1-yl-propoxy)-naphthalene-2-carboxylic acid 1:1 hydrochloride and the respective commercially available amine listed in table 2. The purification was performed with preparative HPLC on reversed phase column material eluting with a gradient formed from acetonitrile/water(0.02% HCL(25%)). The evaporation of the product fractions yielded the respective amides which comprise Example 76 to Example 186 in Table 2:

TABLE 2

| Ex. No. | Systematic Name | MW | Starting Materials | MW found (M + H)+ |
|---|---|---|---|---|
| 76 | 6-(3-piperidin-1-yl-propoxy)-naphthalene-2-carboxylic acid ethylamide 1:1 hydrochloride | 376.93 | 6-(3-piperidin-1-yl-propoxy)-naphthalene-2-carboxylic acid 1:1 hydrochloride (Intermediate M) and ethylamine (commercially available) | 341.3 |
| 77 | 6-(3-piperidin-1-yl-propoxy)-naphthalene-2-carboxylic acid ethyl-methyl-amide 1:1 hydrochloride | 390.95 | 6-(3-piperidin-1-yl-propoxy)-naphthalene-2-carboxylic acid 1:1 hydrochloride (Intermediate M) and ethyl-methylamine (commercially available) | 355.5 |
| 78 | (4,4-difluoro-piperidin-1-yl)-[6-(3-piperidin-1-yl-propoxy)-naphthalen-2-yl]-methanone 1:1 hydrochloride | 452.97 | 6-(3-piperidin-1-yl-propoxy)-naphthalene-2-carboxylic acid 1:1 hydrochloride (Intermediate M) and 4,4-difluoro-piperidine (commercially available) | 417.5 |
| 79 | (2,6-dimethyl-morpholin-4-yl)-[6-(3-piperidin-1-yl-propoxy)-naphthalen-2-yl]-methanone 1:1 hydrochloride | 447.02 | 6-(3-piperidin-1-yl-propoxy)-naphthalene-2-carboxylic acid 1:1 hydrochloride (Intermediate M) and 2,6-dimethyl-morpholine (commercially available) | 411.5 |
| 80 | 6-(3-piperidin-1-yl-propoxy)-naphthalene-2-carboxylic acid methyl-phenethyl-amide 1:1 hydrochloride | 467.05 | 6-(3-piperidin-1-yl-propoxy)-naphthalene-2-carboxylic acid 1:1 hydrochloride (Intermediate M) and methyl-phenethyl-amine (commercially available) | 431.5 |
| 81 | 6-(3-piperidin-1-yl-propoxy)-naphthalene-2-carboxylic acid propylamide 1:1 hydrochloride | 390.95 | 6-(3-piperidin-1-yl-propoxy)-naphthalene-2-carboxylic acid 1:1 hydrochloride (Intermediate M) and propylamine (commercially available) | 355.5 |
| 82 | 6-(3-piperidin-1-yl-propoxy)-naphthalene-2-carboxylic acid methyl-propyl-amide 1:1 hydrochloride | 404.98 | 6-(3-piperidin-1-yl-propoxy)-naphthalene-2-carboxylic acid 1:1 hydrochloride (Intermediate M) and methyl-propyl-amine (commercially available) | 369 |
| 83 | 6-(3-piperidin-1-yl-propoxy)-naphthalene-2-carboxylic acid ethyl-propyl-amide 1:1 hydrochloride | 419.01 | 6-(3-piperidin-1-yl-propoxy)-naphthalene-2-carboxylic acid 1:1 hydrochloride (Intermediate M) and ethyl-propylamine (commercially available) | 383.5 |
| 84 | 6-(3-piperidin-1-yl-propoxy)-naphthalene-2-carboxylic acid cyclohexyl-methyl-amide 1:1 hydrochloride | 445.05 | 6-(3-piperidin-1-yl-propoxy)-naphthalene-2-carboxylic acid 1:1 hydrochloride (Intermediate M) and cyclohexyl-methylamine (commercially available) | 409.4 |
| 85 | (3-hydroxy-pyrrolidin-1-yl)-[6-(3-piperidin-1-yl-propoxy)-naphthalen-2-yl]-methanone 1:1 hydrochloride | 418.96 | 6-(3-piperidin-1-yl-propoxy)-naphthalene-2-carboxylic acid 1:1 hydrochloride (Intermediate M) and 3-hydroxy-pyrrolidine (commercially available) | 383.3 |
| 86 | 6-(3-piperidin-1-yl-propoxy)-naphthalene-2-carboxylic acid benzyl-isopropyl-amide 1:1 hydrochloride | 481.08 | 6-(3-piperidin-1-yl-propoxy)-naphthalene-2-carboxylic acid 1:1 hydrochloride (Intermediate M) and benzyl-isopropyl-amine (commercially available) | 445.4 |
| 87 | 6-(3-piperidin-1-yl-propoxy)-naphthalene-2-carboxylic acid butylamide 1:1 hydrochloride | 404.98 | 6-(3-piperidin-1-yl-propoxy)-naphthalene-2-carboxylic acid 1:1 hydrochloride (Intermediate M) and butylamine (commercially available) | 369.1 |

TABLE 2-continued

| Ex. No. | Systematic Name | MW | Starting Materials | MW found (M + H)+ |
|---|---|---|---|---|
| 88 | azetidin-1-yl-[6-(3-piperidin-1-yl-propoxy)-naphthalen-2-yl]-methanone 1:1 hydrochloride | 388.94 | 6-(3-piperidin-1-yl-propoxy)-naphthalene-2-carboxylic acid 1:1 hydrochloride (Intermediate M) and azetidine (commercially available) | 353.4 |
| 89 | azepan-1-yl-[6-(3-piperidin-1-yl-propoxy)-naphthalen-2-yl]-methanone 1:1 hydrochloride | 431.02 | 6-(3-piperidin-1-yl-propoxy)-naphthalene-2-carboxylic acid 1:1 hydrochloride (Intermediate M) and azepane (commercially available) | 395.5 |
| 90 | 6-(3-piperidin-1-yl-propoxy)-naphthalene-2-carboxylic acid ethyl-(2-methoxy-ethyl)-amide 1:1 hydrochloride | 435.01 | 6-(3-piperidin-1-yl-propoxy)-naphthalene-2-carboxylic acid 1:1 hydrochloride (Intermediate M) and ethyl-(2-methoxy-ethyl)-amine (commercially available) | 399.4 |
| 91 | 6-(3-piperidin-1-yl-propoxy)-naphthalene-2-carboxylic acid cyclopropylmethyl-amide 1:1 hydrochloride | 402.97 | 6-(3-piperidin-1-yl-propoxy)-naphthalene-2-carboxylic acid 1:1 hydrochloride (Intermediate M) and cyclopropylmethyl-amine (commercially available) | 367.4 |
| 92 | 6-(3-piperidin-1-yl-propoxy)-naphthalene-2-carboxylic acid ethyl-isopropyl-amide 1:1 hydrochloride | 419.01 | 6-(3-piperidin-1-yl-propoxy)-naphthalene-2-carboxylic acid 1:1 hydrochloride (Intermediate M) and ethyl-isopropyl-amine (commercially available) | 383.4 |
| 93 | 6-(3-piperidin-1-yl-propoxy)-naphthalene-2-carboxylic acid bis-(2-methoxy-ethyl)-amide 1:1 hydrochloride | 465.03 | 6-(3-piperidin-1-yl-propoxy)-naphthalene-2-carboxylic acid 1:1 hydrochloride (Intermediate M) and bis-(2-methoxy-ethyl)-amine (commercially available) | 429.5 |
| 94 | (3-methoxy-piperidin-1-yl)-[6-(3-piperidin-1-yl-propoxy)-naphthalen-2-yl]-methanone 1:1 hydrochloride | 447.02 | 6-(3-piperidin-1-yl-propoxy)-naphthalene-2-carboxylic acid 1:1 hydrochloride (Intermediate M) and 3-methoxy-piperidine (commercially available) | 411.5 |
| 95 | (4-hydroxymethyl-piperidin-1-yl)-[6-(3-piperidin-1-yl-propoxy)-naphthalen-2-yl]-methanone 1:1 hydrochloride | 447.02 | 6-(3-piperidin-1-yl-propoxy)-naphthalene-2-carboxylic acid 1:1 hydrochloride (Intermediate M) and 4-hydroxymethyl-piperidine (commercially available) | 411.5 |
| 96 | 6-(3-piperidin-1-yl-propoxy)-naphthalene-2-carboxylic acid isobutyl-amide 1:1 hydrochloride | 404.98 | 6-(3-piperidin-1-yl-propoxy)-naphthalene-2-carboxylic acid 1:1 hydrochloride (Intermediate M) and isobutylamine (commercially available) | 369.1 |
| 97 | 6-(3-piperidin-1-yl-propoxy)-naphthalene-2-carboxylic acid cyclohexyl-ethyl-amide 1:1 hydrochloride | 459.07 | 6-(3-piperidin-1-yl-propoxy)-naphthalene-2-carboxylic acid 1:1 hydrochloride (Intermediate M) and cyclohexyl-ethyl-amine (commercially available) | 423.5 |
| 98 | 6-(3-piperidin-1-yl-propoxy)-naphthalene-2-carboxylic acid cyclopropylamide 1:1 hydrochloride | 388.94 | 6-(3-piperidin-1-yl-propoxy)-naphthalene-2-carboxylic acid 1:1 hydrochloride (Intermediate M) and cyclopropylamine (commercially available) | 353.4 |
| 99 | 6-(3-piperidin-1-yl-propoxy)-naphthalene-2-carboxylic acid (2-methoxy-ethyl)-amide 1:1 hydrochloride | 406.95 | 6-(3-piperidin-1-yl-propoxy)-naphthalene-2-carboxylic acid 1:1 hydrochloride (Intermediate M) and (2-methoxy-ethyl)-amine (commercially available) | 371.4 |
| 100 | 6-(3-piperidin-1-yl-propoxy)-naphthalene-2-carboxylic acid [2-(3,4-dimethoxy-phenyl)-ethyl]- | 527.1 | 6-(3-piperidin-1-yl-propoxy)-naphthalene-2-carboxylic acid 1:1 hydrochloride (Intermediate M) and | 491.3 |

TABLE 2-continued

| Ex. No. | Systematic Name | MW | Starting Materials | MW found (M + H)+ |
|---|---|---|---|---|
| | methyl-amide 1:1 hydrochloride | | 2-(3,4-dimethoxy-phenyl)-ethyl]-methyl-amine (commercially available) | |
| 101 | 6-(3-piperidin-1-yl-propoxy)-naphthalene-2-carboxylic acid ethyl-(2-fluoro-benzyl)-amide 1:1 hydrochloride | 485.04 | 6-(3-piperidin-1-yl-propoxy)-naphthalene-2-carboxylic acid 1:1 hydrochloride (Intermediate M) and 2-fluoro-benzylamine (commercially available) | 449.4 |
| 102 | (2-methyl-piperidin-1-yl)-[6-(3-piperidin-1-yl-propoxy)-naphthalen-2-yl]-methanone 1:1 hydrochloride | 431.02 | 6-(3-piperidin-1-yl-propoxy)-naphthalene-2-carboxylic acid 1:1 hydrochloride (Intermediate M) and 2-methyl-piperidine (commercially available) | 395.5 |
| 103 | (4-benzyl-piperazin-1-yl)-[6-(3-piperidin-1-yl-propoxy)-naphthalen-2-yl]-methanone 1:2 hydrochloride | 544.57 | 6-(3-piperidin-1-yl-propoxy)-naphthalene-2-carboxylic acid 1:1 hydrochloride (Intermediate M) and 4-benzyl-piperazine (commercially available) | 472.5 |
| 104 | (3-Methyl-piperidin-1-yl)-[6-(3-piperidin-1-yl-propoxy)-naphthalen-2-yl]-methanone 1:1 hydrochloride | 431.02 | 6-(3-piperidin-1-yl-propoxy)-naphthalene-2-carboxylic acid 1:1 hydrochloride (Intermediate M) and 3-methyl-piperidine (commercially available) | 395.5 |
| 105 | 6-(3-piperidin-1-yl-propoxy)-naphthalene-2-carboxylic acid ethyl-pyridin-4-ylmethyl-amide 1:1 hydrochloride | 468.04 | 6-(3-piperidin-1-yl-propoxy)-naphthalene-2-carboxylic acid 1:1 hydrochloride (Intermediate M) and ethyl-pyridin-4-ylmethyl-amine (commercially available) | 432.5 |
| 106 | 6-(3-piperidin-1-yl-propoxy)-naphthalene-2-carboxylic acid cyclobutylamide 1:1 hydrochloride | 402.97 | 6-(3-piperidin-1-yl-propoxy)-naphthalene-2-carboxylic acid 1:1 hydrochloride (Intermediate M) and cyclobutylamine (commercially available) | 367 |
| 107 | (4-phenyl-piperazin-1-yl)-[6-(3-piperidin-1-yl-propoxy)-naphthalen-2-yl]-methanone 1:2 hydrochloride | 530.54 | 6-(3-piperidin-1-yl-propoxy)-naphthalene-2-carboxylic acid 1:1 hydrochloride (Intermediate M) and 4-phenyl-piperazine (commercially available) | 458.3 |
| 108 | 6-(3-piperidin-1-yl-propoxy)-naphthalene-2-carboxylic acid (2-thiophen-2-yl-ethyl)-amide 1:1 hydrochloride | 459.05 | 6-(3-piperidin-1-yl-propoxy)-naphthalene-2-carboxylic acid 1:1 hydrochloride (Intermediate M) and 2-thiophen-2-yl-ethyl-amine (commercially available) | 423.4 |
| 109 | 6-(3-piperidin-1-yl-propoxy)-naphthalene-2-carboxylic acid (3-methoxy-propyl)-amide 1:1 hydrochloride | 420.98 | 6-(3-piperidin-1-yl-propoxy)-naphthalene-2-carboxylic acid 1:1 hydrochloride (Intermediate M) and 3-methoxy-propyl-amine (commercially available) | 385.1 |
| 110 | 6-(3-piperidin-1-yl-propoxy)-naphthalene-2-carboxylic acid (3-methyl-thiophen-2-ylmethyl)-amide 1:1 hydrochloride | 459.05 | 6-(3-piperidin-1-yl-propoxy)-naphthalene-2-carboxylic acid 1:1 hydrochloride (Intermediate M) and 3-methyl-thiophen-2-ylmethyl-amine (commercially available) | 423.4 |
| 111 | 6-(3-piperidin-1-yl-propoxy)-naphthalene-2-carboxylic acid [2-(2-methyl-piperidin-1-yl)-ethyl]-amide 1:2 hydrochloride | 510.55 | 6-(3-piperidin-1-yl-propoxy)-naphthalene-2-carboxylic acid 1:1 hydrochloride (Intermediate M) and 2-(2-methyl-piperidin-1-yl)-ethyl-amine (commercially available) | 438.5 |
| 112 | (1,3-dihydro-isoindol-2-yl)-[6-(3-piperidin-1-yl-propoxy)-naphthalen-2-yl]-methanone 1:1 hydrochloride | 451.01 | 6-(3-piperidin-1-yl-propoxy)-naphthalene-2-carboxylic acid 1:1 hydrochloride (Intermediate M) and 1,3-dihydro-isoindole (commercially available) | 415.5 |

TABLE 2-continued

| Ex. No. | Systematic Name | MW | Starting Materials | MW found (M + H)+ |
|---|---|---|---|---|
| 113 | 6-(3-piperidin-1-yl-propoxy)-naphthalene-2-carboxylic acid (2-morpholin-4-yl-ethyl)-amide 1:2 hydrochloride | 498.49 | 6-(3-piperidin-1-yl-propoxy)-naphthalene-2-carboxylic acid 1:1 hydrochloride (Intermediate M) and 2-morpholin-4-yl-ethyl-amine (commercially available) | 426.5 |
| 114 | 6-(3-piperidin-1-yl-propoxy)-naphthalene-2-carboxylic acid (thiophen-2-ylmethyl)-amide 1:1 hydrochloride | 445.02 | 6-(3-piperidin-1-yl-propoxy)-naphthalene-2-carboxylic acid 1:1 hydrochloride (Intermediate M) and thiophen-2-ylmethyl-amine (commercially available) | 409.4 |
| 115 | (3,6-dihydro-2H-pyridin-1-yl)-[6-(3-piperidin-1-yl-propoxy)-naphthalen-2-yl]-methanone 1:1 hydrochloride | 414.98 | 6-(3-piperidin-1-yl-propoxy)-naphthalene-2-carboxylic acid 1:1 hydrochloride (Intermediate M) and 3,6-dihydro-2H-pyridine (commercially available) | 379.4 |
| 116 | [6-(3-piperidin-1-yl-propoxy)-naphthalen-2-yl]-(3-pyridin-2-yl-pyrrolidin-1-yl)-methanone 1:1 hydrochloride | 480.05 | 6-(3-piperidin-1-yl-propoxy)-naphthalene-2-carboxylic acid 1:1 hydrochloride (Intermediate M) and 3-pyridin-2-yl-pyrrolidine (commercially available) | 444.5 |
| 117 | 6-(3-piperidin-1-yl-propoxy)-naphthalene-2-carboxylic acid (2-dimethylamino-ethyl)-ethyl-amide 1:2 hydrochloride | 484.51 | 6-(3-piperidin-1-yl-propoxy)-naphthalene-2-carboxylic acid 1:1 hydrochloride (Intermediate M) and 2-dimethylamino-ethyl-ethyl-amine (commercially available) | 412.5 |
| 118 | (4-fluoro-piperidin-1-yl)-[6-(3-piperidin-1-yl-propoxy)-naphthalen-2-yl]-methanone; 1:1 hydrochloride | 434.98 | 6-(3-piperidin-1-yl-propoxy)-naphthalene-2-carboxylic acid 1:1 hydrochloride (Intermediate M) and 4-fluoro-piperidine (commercially available) | 399.3 |
| 119 | (4-benzyl-piperidin-1-yl)-[6-(3-piperidin-1-yl-propoxy)-naphthalen-2-yl]-methanone 1:1 hydrochloride | 507.12 | 6-(3-piperidin-1-yl-propoxy)-naphthalene-2-carboxylic acid 1:1 hydrochloride (Intermediate M) and 4-benzyl-piperidine (commercially available) | 471.5 |
| 120 | (4-methyl-piperazin-1-yl)-[6-(3-piperidin-1-yl-propoxy)-naphthalen-2-yl]-methanone 1:2 hydrochloride | 468.47 | 6-(3-piperidin-1-yl-propoxy)-naphthalene-2-carboxylic acid 1:1 hydrochloride (Intermediate M) and 4-methyl-piperazine (commercially available) | 396.4 |
| 121 | 6-(3-piperidin-1-yl-propoxy)-naphthalene-2-carboxylic acid cycloheptylamide 1:1 hydrochloride | 445.05 | 6-(3-piperidin-1-yl-propoxy)-naphthalene-2-carboxylic acid 1:1 hydrochloride (Intermediate M) and cycloheptylamine (commercially available) | 409.4 |
| 122 | 6-(3-piperidin-1-yl-propoxy)-naphthalene-2-carboxylic acid cyclopentylamide 1:1 hydrochloride | 416.99 | 6-(3-piperidin-1-yl-propoxy)-naphthalene-2-carboxylic acid 1:1 hydrochloride (Intermediate M) and cyclopentylamine (commercially available) | 381.5 |
| 123 | (4-hydroxy-piperidin-1-yl)-[6-(3-piperidin-1-yl-propoxy)-naphthalen-2-yl]-methanone 1:1 hydrochloride | 432.99 | 6-(3-piperidin-1-yl-propoxy)-naphthalene-2-carboxylic acid 1:1 hydrochloride (Intermediate M) and 4-hydroxy-piperidine (commercially available) | 397.3 |
| 124 | 1-[6-(3-piperidin-1-yl-propoxy)-naphthalene-2-carbonyl]-piperidine-4-carboxylic acid amide 1:1 hydrochloride | 460.02 | 6-(3-piperidin-1-yl-propoxy)-naphthalene-2-carboxylic acid 1:1 hydrochloride (Intermediate M) and piperidine-4-carboxylic acid amide (commercially available) | 424.5 |

TABLE 2-continued

| Ex. No. | Systematic Name | MW | Starting Materials | MW found $(M + H)^+$ |
|---|---|---|---|---|
| 125 | (3-hydroxymethyl-piperidin-1-yl)-[6-(3-piperidin-1-yl-propoxy)-naphthalen-2-yl]-methanone 1:1 hydrochloride | 447.02 | 6-(3-piperidin-1-yl-propoxy)-naphthalene-2-carboxylic acid 1:1 hydrochloride (Intermediate M) and 3-hydroxymethyl-piperidine (commercially available) | 411.5 |
| 126 | 6-(3-piperidin-1-yl-propoxy)-naphthalene-2-carboxylic acid cyclohexylamide 1:1 hydrochloride | 431.02 | 6-(3-piperidin-1-yl-propoxy)-naphthalene-2-carboxylic acid 1:1 hydrochloride (Intermediate M) and cyclohexylamine (commercially available) | 395.5 |
| 127 | (4-bromo-piperidin-1-yl)-[6-(3-piperidin-1-yl-propoxy)-naphthalen-2-yl]-methanone 1:1 hydrochloride | 495.89 | 6-(3-piperidin-1-yl-propoxy)-naphthalene-2-carboxylic acid 1:1 hydrochloride (Intermediate M) and 4-bromo-piperidine (commercially available) | 459.5 |
| 128 | (4-benzyl-4-hydroxy-piperidin-1-yl)-[6-(3-piperidin-1-yl-propoxy)-naphthalen-2-yl]-methanone 1:1 hydrochloride | 523.12 | 6-(3-piperidin-1-yl-propoxy)-naphthalene-2-carboxylic acid 1:1 hydrochloride (Intermediate M) and 4-benzyl-4-hydroxy-piperidine (commercially available) | 487.6 |
| 129 | 6-(3-piperidin-1-yl-propoxy)-naphthalene-2-carboxylic acid [3-(1-hydroxy-ethyl)-phenyl]-amide 1:1 hydrochloride | 469.02 | 6-(3-piperidin-1-yl-propoxy)-naphthalene-2-carboxylic acid 1:1 hydrochloride (Intermediate M) and 3-(1-hydroxy-ethyl)-phenyl]-amine (commercially available) | 433.4 |
| 130 | (3-methanesulfonyl-pyrrolidin-1-yl)-[6-(3-piperidin-1-yl-propoxy)-naphthalen-2-yl]-methanone 1:1 hydrochloride | 481.05 | 6-(3-piperidin-1-yl-propoxy)-naphthalene-2-carboxylic acid 1:1 hydrochloride (Intermediate M) and 3-methanesulfonyl-pyrrolidine (commercially available) | 445.4 |
| 131 | (2-isopropyl-pyrrolidin-1-yl)-[6-(3-piperidin-1-yl-propoxy)-naphthalen-2-yl]-methanone 1:1 hydrochloride | 445.05 | 6-(3-piperidin-1-yl-propoxy)-naphthalene-2-carboxylic acid 1:1 hydrochloride (Intermediate M) and 2-isopropyl-pyrrolidine (commercially available) | 409.4 |
| 132 | 6-(3-piperidin-1-yl-propoxy)-naphthalene-2-carboxylic acid (3,4-dimethyl-phenyl)-amide 1:1 hydrochloride | 453.03 | 6-(3-piperidin-1-yl-propoxy)-naphthalene-2-carboxylic acid 1:1 hydrochloride (Intermediate M) and 3,4-dimethyl-phenyl-amine (commercially available) | 417.5 |
| 133 | (3-dimethylamino-pyrrolidin-1-yl)-[6-(3-piperidin-1-yl-propoxy)-naphthalen-2-yl]-methanone 1:2 hydrochloride | 482.5 | 6-(3-piperidin-1-yl-propoxy)-naphthalene-2-carboxylic acid 1:1 hydrochloride (Intermediate M) and 3-dimethylamino-pyrrolidine (commercially available) | 410.5 |
| 134 | 2,2,2-trifluoro-N-{1-[6-(3-piperidin-1-yl-propoxy)-naphthalene-2-carbonyl]-pyrrolidin-3-yl}-acetamide 1:1 hydrochloride | 513.99 | 6-(3-piperidin-1-yl-propoxy)-naphthalene-2-carboxylic acid 1:1 hydrochloride (Intermediate M) and 2,2,2-trifluoro-N-pyrrolidin-3-yl-acetamide (commercially available) | 478.5 |
| 135 | 6-(3-piperidin-1-yl-propoxy)-naphthalene-2-carboxylic acid methyl-(1-methyl-pyrrolidin-3-yl)-amide 1:2 hydrochloride | 482.5 | 6-(3-piperidin-1-yl-propoxy)-naphthalene-2-carboxylic acid 1:1 hydrochloride (Intermediate M) and 1-methyl-pyrrolidin-3-yl-amine (commercially available) | 410.5 |
| 136 | [6-(3-piperidin-1-yl-propoxy)-naphthalen-2-yl]-(4-trifluoromethyl-piperidin-1-yl)-methanone 1:1 hydrochloride | 484.99 | 6-(3-piperidin-1-yl-propoxy)-naphthalene-2-carboxylic acid 1:1 hydrochloride (Intermediate M) and 4-trifluoromethyl-piperidine (commercially available) | 449.4 |
| 137 | [6-(1-isopropyl-piperidin-4-yloxy)-naphthalen-2-yl]-(4-methyl-piperazin-1-yl)- | 468.47 | 6-(1-isopropyl-piperidin-4-yloxy)-naphthalene-2-carboxylic acid 1:1 hydrochloride | 396.5 |

TABLE 2-continued

| Ex. No. | Systematic Name | MW | Starting Materials | MW found (M + H)+ |
|---|---|---|---|---|
| | methanone 1:2 hydrochloride | | (Intermediate O) and 4-methyl-piperazine (commercially available) | |
| 138 | [6-(1-isopropyl-piperidin-4-yloxy)-naphthalen-2-yl]-(2-isopropyl-pyrrolidin-1-yl)-methanone 1:1 hydrochloride | 445.05 | 6-(1-isopropyl-piperidin-4-yloxy)-naphthalene-2-carboxylic acid 1:1 hydrochloride (Intermediate O) and 2-isopropyl-pyrrolidine (commercially available) | 409.5 |
| 139 | (4-benzyl-piperidin-1-yl)-[6-(1-isopropyl-piperidin-4-yloxy)-naphthalen-2-yl]-methanone 1:1 hydrochloride | 507.12 | 6-(1-isopropyl-piperidin-4-yloxy)-naphthalene-2-carboxylic acid 1:1 hydrochloride (Intermediate O) and 4-benzyl-piperidine (commercially available) | 471.6 |
| 140 | (4-isopropyl-piperazin-1-yl)-[6-(1-isopropyl-piperidin-4-yloxy)-naphthalen-2-yl]-methanone 1:2 hydrochloride | 460.06 | 6-(1-isopropyl-piperidin-4-yloxy)-naphthalene-2-carboxylic acid 1:1 hydrochloride (Intermediate O) and 4-isopropyl-piperazine (commercially available) | 424.5 |
| 141 | (4-hydroxymethyl-piperidin-1-yl)-[6-(1-isopropyl-piperidin-4-yloxy)-naphthalen-2-yl]-methanone 1:1 hydrochloride | 447.02 | 6-(1-isopropyl-piperidin-4-yloxy)-naphthalene-2-carboxylic acid 1:1 hydrochloride (Intermediate O) and 4-hydroxymethyl-piperidine (commercially available) | 411.5 |
| 142 | 6-(1-isopropyl-piperidin-4-yloxy)-naphthalene-2-carboxylic acid (2-methoxy-ethyl)-amide 1:1 hydrochloride | 406.95 | 6-(1-isopropyl-piperidin-4-yloxy)-naphthalene-2-carboxylic acid 1:1 hydrochloride (Intermediate O) and 2-methoxy-ethyl-amine (commercially available) | 371.4 |
| 143 | 6-(1-isopropyl-piperidin-4-yloxy)-naphthalene-2-carboxylic acid 4-methyl-benzylamide 1:1 hydrochloride | 453.03 | 6-(1-isopropyl-piperidin-4-yloxy)-naphthalene-2-carboxylic acid 1:1 hydrochloride (Intermediate O) and 4-methyl-benzylamine (commercially available) | 417.4 |
| 144 | [6-(1-isopropyl-piperidin-4-yloxy)-naphthalen-2-yl]-(4-trifluoromethyl-piperidin-1-yl)-methanone 1:1 hydrochloride | 484.99 | 6-(1-isopropyl-piperidin-4-yloxy)-naphthalene-2-carboxylic acid 1:1 hydrochloride (Intermediate O) and 4-trifluoromethyl-piperidine (commercially available) | 449.4 |
| 145 | (4-fluoro-piperidin-1-yl)-[6-(1-isopropyl-piperidin-4-yloxy)-naphthalen-2-yl]-methanone 1:1 hydrochloride | 434.98 | 6-(1-isopropyl-piperidin-4-yloxy)-naphthalene-2-carboxylic acid 1:1 hydrochloride (Intermediate O) and 4-fluoro-piperidine (commercially available) | 399.3 |
| 146 | (4,4-difluoro-piperidin-1-yl)-[6-(1-isopropyl-piperidin-4-yloxy)-naphthalen-2-yl]-methanone 1:1 hydrochloride | 452.97 | 6-(1-isopropyl-piperidin-4-yloxy)-naphthalene-2-carboxylic acid 1:1 hydrochloride (Intermediate O) and 4,4-difluoro-piperidine (commercially available) | 417.5 |
| 147 | 6-(1-isopropyl-piperidin-4-yloxy)-naphthalene-2-carboxylic acid cyclopropylmethyl-amide 1:1 hydrochloride | 402.97 | 6-(1-isopropyl-piperidin-4-yloxy)-naphthalene-2-carboxylic acid 1:1 hydrochloride (Intermediate O) and cyclopropylmethyl-amine (commercially available) | 367.3 |
| 148 | 6-(1-isopropyl-piperidin-4-yloxy)-naphthalene-2-carboxylic acid (2-methylsulfanyl-ethyl)-amide 1:1 hydrochloride | 423.02 | 6-(1-isopropyl-piperidin-4-yloxy)-naphthalene-2-carboxylic acid 1:1 hydrochloride (Intermediate O) and 2-methylsulfanyl-ethyl-amine (commercially available) | 387.4 |
| 149 | 6-(1-isopropyl-piperidin-4-yloxy)-naphthalene-2-carboxylic acid 4-fluoro-benzylamide 1:1 hydrochloride | 456.99 | 6-(1-isopropyl-piperidin-4-yloxy)-naphthalene-2-carboxylic acid 1:1 hydrochloride (Intermediate O) and 4-fluoro-benzylamine (commercially available) | 421.1 |

TABLE 2-continued

| Ex. No. | Systematic Name | MW | Starting Materials | MW found (M + H)+ |
|---|---|---|---|---|
| 150 | [6-(1-isopropyl-piperidin-4-yloxy)-naphthalen-2-yl]-(3-methoxy-piperidin-1-yl)-methanone 1:1 hydrochloride | 447.02 | 6-(1-isopropyl-piperidin-4-yloxy)-naphthalene-2-carboxylic acid 1:1 hydrochloride (Intermediate O) and 3-methoxy-piperidine (commercially available) | 411.5 |
| 151 | 6-(1-isopropyl-piperidin-4-yloxy)-naphthalene-2-carboxylic acid phenethyl-amide; 1:1 hydrochloride | 453.03 | 6-(1-isopropyl-piperidin-4-yloxy)-naphthalene-2-carboxylic acid 1:1 hydrochloride (Intermediate O) and phenethyl-amine (commercially available) | 417.5 |
| 152 | (3-hydroxy-pyrrolidin-1-yl)-[6-(1-isopropyl-piperidin-4-yloxy)-naphthalen-2-yl]-methanone 1:1 hydrochloride | 418.96 | 6-(1-isopropyl-piperidin-4-yloxy)-naphthalene-2-carboxylic acid 1:1 hydrochloride (Intermediate O) and 3-hydroxy-pyrrolidine (commercially available) | 383.4 |
| 153 | (4-hydroxy-piperidin-1-yl)-[6-(1-isopropyl-piperidin-4-yloxy)-naphthalen-2-yl]-methanone 1:1 hydrochloride | 432.99 | 6-(1-isopropyl-piperidin-4-yloxy)-naphthalene-2-carboxylic acid 1:1 hydrochloride (Intermediate O) and 4-hydroxy-piperidine (commercially available) | 397.4 |
| 154 | 6-(1-isopropyl-piperidin-4-yloxy)-naphthalene-2-carboxylic acid (3-dimethylamino-propyl)-amide 1:2 hydrochloride | 470.48 | 6-(1-isopropyl-piperidin-4-yloxy)-naphthalene-2-carboxylic acid 1:1 hydrochloride (Intermediate O) and 3-dimethylamino-propyl-amine (commercially available) | 398.1 |
| 155 | 6-(1-isopropyl-piperidin-4-yloxy)-naphthalene-2-carboxylic acid ethyl-(2-methoxy-ethyl)-amide 1:1 hydrochloride | 435.01 | 6-(1-isopropyl-piperidin-4-yloxy)-naphthalene-2-carboxylic acid 1:1 hydrochloride (Intermediate O) and ethyl-(2-methoxy-ethyl)-amine (commercially available) | 399.3 |
| 156 | 6-(1-isopropyl-piperidin-4-yloxy)-naphthalene-2-carboxylic acid (2-morpholin-4-yl-ethyl)-amide 1:2 hydrochloride | 498.49 | 6-(1-isopropyl-piperidin-4-yloxy)-naphthalene-2-carboxylic acid 1:1 hydrochloride (Intermediate O) and 2-morpholin-4-yl-ethyl-amine (commercially available) | 426.4 |
| 157 | 6-(1-isopropyl-piperidin-4-yloxy)-naphthalene-2-carboxylic acid (2-piperidin-1-yl-ethyl)-amide 1:2 hydrochloride | 496.52 | 6-(1-isopropyl-piperidin-4-yloxy)-naphthalene-2-carboxylic acid 1:1 hydrochloride (Intermediate O) and 2-piperidin-1-yl-ethyl-amine (commercially available) | 424.4 |
| 158 | (4-benzyl-piperazin-1-yl)-[6-(1-isopropyl-piperidin-4-yloxy)-naphthalen-2-yl]-methanone 1:2 hydrochloride | 544.57 | 6-(1-isopropyl-piperidin-4-yloxy)-naphthalene-2-carboxylic acid 1:1 hydrochloride (Intermediate O) and 4-benzyl-piperazine (commercially available) | 472.5 |
| 159 | 6-(1-isopropyl-piperidin-4-yloxy)-naphthalene-2-carboxylic acid isopropyl-methyl-amide 1:1 hydrochloride | 404.98 | 6-(1-isopropyl-piperidin-4-yloxy)-naphthalene-2-carboxylic acid 1:1 hydrochloride (Intermediate O) and isopropyl-methyl-amine (commercially available) | 369.4 |
| 160 | azepan-1-yl-[6-(1-isopropyl-piperidin-4-yloxy)-naphthalen-2-yl]-methanone 1:1 hydrochloride | 431.02 | 6-(1-isopropyl-piperidin-4-yloxy)-naphthalene-2-carboxylic acid 1:1 hydrochloride (Intermediate O) and azepane (commercially available) | 395.5 |
| 161 | 6-(1-isopropyl-piperidin-4-yloxy)-naphthalene-2-carboxylic acid isobutyl-amide 1:1 hydrochloride | 404.98 | 6-(1-isopropyl-piperidin-4-yloxy)-naphthalene-2-carboxylic acid 1:1 hydrochloride (Intermediate O) and isobutylamine (commercially available) | 369.3 |
| 162 | 6-(1-isopropyl-piperidin-4-yloxy)-naphthalene-2-carboxylic acid cyclohexyl- | 445.05 | 6-(1-isopropyl-piperidin-4-yloxy)-naphthalene-2-carboxylic acid 1:1 hydrochloride | 409.3 |

TABLE 2-continued

| Ex. No. | Systematic Name | MW | Starting Materials | MW found (M + H)+ |
|---|---|---|---|---|
| | methyl-amide 1:1 hydrochloride | | (Intermediate O) and cyclohexyl-methyl-amine (commercially available) | |
| 163 | 6-(1-isopropyl-piperidin-4-yloxy)-naphthalene-2-carboxylic acid ethyl-pyridin-4-ylmethyl-amide 1:1 hydrochloride | 468.04 | 6-(1-isopropyl-piperidin-4-yloxy)-naphthalene-2-carboxylic acid 1:1 hydrochloride (Intermediate O) and ethyl-pyridin-4-ylmethyl-amine (commercially available) | 432.5 |
| 164 | 6-(1-isopropyl-piperidin-4-yloxy)-naphthalene-2-carboxylic acid methyl-phenethyl-amide 1:1 hydrochloride | 467.05 | 6-(1-isopropyl-piperidin-4-yloxy)-naphthalene-2-carboxylic acid 1:1 hydrochloride (Intermediate O) and methyl-phenethyl-amine (commercially available) | 431.5 |
| 165 | 6-(1-isopropyl-piperidin-4-yloxy)-naphthalene-2-carboxylic acid methyl-propyl-amide 1:1 hydrochloride | 404.98 | 6-(1-isopropyl-piperidin-4-yloxy)-naphthalene-2-carboxylic acid 1:1 hydrochloride (Intermediate O) and methyl-propyl-amine (commercially available) | 369.1 |
| 166 | 6-(1-isopropyl-piperidin-4-yloxy)-naphthalene-2-carboxylic acid cyclopropylmethyl-propyl-amide 1:1 hydrochloride | 445.05 | 6-(1-isopropyl-piperidin-4-yloxy)-naphthalene-2-carboxylic acid 1:1 hydrochloride (Intermediate O) and cyclopropylmethyl-propyl-amine (commercially available) | 409.3 |
| 167 | 6-(1-isopropyl-piperidin-4-yloxy)-naphthalene-2-carboxylic acid (3-methoxy-propyl)-amide 1:1 hydrochloride | 420.98 | 6-(1-isopropyl-piperidin-4-yloxy)-naphthalene-2-carboxylic acid 1:1 hydrochloride (Intermediate O) and 3-methoxy-propyl-amine (commercially available) | 385.5 |
| 168 | 6-(1-isopropyl-piperidin-4-yloxy)-naphthalene-2-carboxylic acid propylamide 1:1 hydrochloride | 390.95 | 6-(1-isopropyl-piperidin-4-yloxy)-naphthalene-2-carboxylic acid 1:1 hydrochloride (Intermediate O) and propylamine (commercially available) | 355.5 |
| 169 | 6-(1-isopropyl-piperidin-4-yloxy)-naphthalene-2-carboxylic acid cyclopentylamide 1:1 hydrochloride | 416.99 | 6-(1-isopropyl-piperidin-4-yloxy)-naphthalene-2-carboxylic acid 1:1 hydrochloride (Intermediate O) and cyclopentylamine (commercially available) | 381.5 |
| 170 | 6-(1-isopropyl-piperidin-4-yloxy)-naphthalene-2-carboxylic acid cyclohexylamide 1:1 hydrochloride | 431.02 | 6-(1-isopropyl-piperidin-4-yloxy)-naphthalene-2-carboxylic acid 1:1 hydrochloride (Intermediate O) and cyclohexylamine (commercially available) | 395.5 |
| 171 | 6-(1-isopropyl-piperidin-4-yloxy)-naphthalene-2-carboxylic acid ethyl-methyl-amide; 1:1 hydrochloride | 390.95 | 6-(1-isopropyl-piperidin-4-yloxy)-naphthalene-2-carboxylic acid 1:1 hydrochloride (Intermediate O) and ethyl-methyl-amine (commercially available) | 355.5 |
| 172 | 6-(1-isopropyl-piperidin-4-yloxy)-naphthalene-2-carboxylic acid tert-butylamide 1:1 hydrochloride | 404.98 | 6-(1-isopropyl-piperidin-4-yloxy)-naphthalene-2-carboxylic acid 1:1 hydrochloride (Intermediate O) and tert-butylamine (commercially available) | 369.5 |
| 173 | 6-(1-isopropyl-piperidin-4-yloxy)-naphthalene-2-carboxylic acid cyclopropylamide 1:1 hydrochloride | 388.94 | 6-(1-isopropyl-piperidin-4-yloxy)-naphthalene-2-carboxylic acid 1:1 hydrochloride (Intermediate O) and cyclopropylamine (commercially available) | 353.4 |
| 174 | 6-(1-isopropyl-piperidin-4-yloxy)-naphthalene-2-carboxylic acid isopropylamide 1:1 hydrochloride | 390.95 | 6-(1-isopropyl-piperidin-4-yloxy)-naphthalene-2-carboxylic acid 1:1 hydrochloride (Intermediate O) and isopropylamine (commercially available) | 355.5 |

TABLE 2-continued

| Ex. No. | Systematic Name | MW | Starting Materials | MW found $(M + H)^+$ |
|---|---|---|---|---|
| 175 | 6-(1-isopropyl-piperidin-4-yloxy)-naphthalene-2-carboxylic acid diethylamide 1:1 hydrochloride | 404.98 | 6-(1-isopropyl-piperidin-4-yloxy)-naphthalene-2-carboxylic acid 1:1 hydrochloride (Intermediate O) and diethylamine (commercially available) | 369.1 |
| 176 | 6-(1-isopropyl-piperidin-4-yloxy)-naphthalene-2-carboxylic acid methyl-(2-pyridin-2-yl-ethyl)-amide 1:1 hydrochloride | 468.04 | 6-(1-isopropyl-piperidin-4-yloxy)-naphthalene-2-carboxylic acid 1:1 hydrochloride (Intermediate O) and methyl-(2-pyridin-2-yl-ethyl-amine (commercially available) | 432.5 |
| 177 | 6-(1-isopropyl-piperidin-4-yloxy)-naphthalene-2-carboxylic acid benzyl-ethyl-amide 1:1 hydrochloride | 467.05 | 6-(1-isopropyl-piperidin-4-yloxy)-naphthalene-2-carboxylic acid 1:1 hydrochloride (Intermediate O) and benzyl-ethyl-amine (commercially available) | 431.5 |
| 178 | [6-(1-isopropyl-piperidin-4-yloxy)-naphthalen-2-yl]-(2-methyl-piperidin-1-yl)-methanone 1:1 hydrochloride | 431.02 | 6-(1-isopropyl-piperidin-4-yloxy)-naphthalene-2-carboxylic acid 1:1 hydrochloride (Intermediate O) and 2-methyl-piperidine (commercially available) | 395.5 |
| 179 | (3-dimethylamino-pyrrolidin-1-yl)-[6-(1-isopropyl-piperidin-4-yloxy)-naphthalen-2-yl]-methanone 1:2 hydrochloride | 482.5 | 6-(1-isopropyl-piperidin-4-yloxy)-naphthalene-2-carboxylic acid 1:1 hydrochloride (Intermediate O) and 3-dimethylamino-pyrrolidine (commercially available) | 410.4 |
| 180 | 6-(1-isopropyl-piperidin-4-yloxy)-naphthalene-2-carboxylic acid methyl-(1-methyl-pyrrolidin-3-yl)-amide 1:2 hydrochloride | 482.5 | 6-(1-isopropyl-piperidin-4-yloxy)-naphthalene-2-carboxylic acid 1:1 hydrochloride (Intermediate O) and methyl-(1-methyl-pyrrolidin-3-yl)-amine (commercially available) | 410.5 |
| 181 | [6-(1-isopropyl-piperidin-4-yloxy)-naphthalen-2-yl]-(3-methanesulfonyl-pyrrolidin-1-yl)-methanone 1:1 hydrochloride | 481.05 | 6-(1-isopropyl-piperidin-4-yloxy)-naphthalene-2-carboxylic acid 1:1 hydrochloride (Intermediate O) and 3-methanesulfonyl-pyrrolidine (commercially available) | 445.4 |
| 182 | 6-(1-isopropyl-piperidin-4-yloxy)-naphthalene-2-carboxylic acid cycloheptylamide 1:1 hydrochloride | 445.05 | 6-(1-isopropyl-piperidin-4-yloxy)-naphthalene-2-carboxylic acid 1:1 hydrochloride (Intermediate O) and cycloheptylamine (commercially available) | 409.3 |
| 183 | 2,2,2-trifluoro-N-{1-[6-(1-isopropyl-piperidin-4-yloxy)-naphthalene-2-carbonyl]-pyrrolidin-3-yl}-acetamide 1:1 hydrochloride | 513.99 | 6-(1-isopropyl-piperidin-4-yloxy)-naphthalene-2-carboxylic acid 1:1 hydrochloride (Intermediate O) and 2,2,2-trifluoro-N-pyrrolidin-3-yl-acetamide (commercially available) | 478.4 |
| 184 | 1-[6-(1-isopropyl-piperidin-4-yloxy)-naphthalene-2-carbonyl]-piperidine-4-carboxylic acid amide 1:1 hydrochloride | 460.02 | 6-(1-isopropyl-piperidin-4-yloxy)-naphthalene-2-carboxylic acid 1:1 hydrochloride (Intermediate O) and piperidine-4-carboxylic acid amine (commercially available) | 424.5 |
| 185 | (4-cyclopentyl-piperazin-1-yl)-[6-(1-isopropyl-piperidin-4-yloxy)-naphthalen-2-yl]-methanone 1:2 hydrochloride | 522.56 | 6-(1-isopropyl-piperidin-4-yloxy)-naphthalene-2-carboxylic acid 1:1 hydrochloride (Intermediate O) and 4-cyclopentyl-piperazine (commercially available) | 450.5 |
| 186 | [6-(1-isopropyl-piperidin-4-yloxy)-naphthalen-2-yl]-[4-(4-trifluoromethyl-phenyl)-piperazin-1-yl]-methanone 1:1 hydrochloride | 598.54 | 6-(1-isopropyl-piperidin-4-yloxy)-naphthalene-2-carboxylic acid 1:1 hydrochloride (Intermediate O) and 4-(4-trifluoromethyl-phenyl)-piperazine (commercially available) | 526.5 |

Example 187

[6-(1-Isopropyl-piperidin-4-yloxy)-naphthalen-2-yl]-((R)-2-methyl-pyrrolidin-1-yl)-methanone The racemic (2-methyl-pyrrolidin-1-yl)-[6-(3-piperidin-1-yl-propoxy)-naphthalen-2-yl]-methanone 1:1 hydrochloride (Example 6) was resolved on a ChiralPack AD® column (Daicel Chemical Industries Ltd.) eluting with heptane/ethanol 85/15. The product fractions were evaporated, yielding to 175 mg (38%) of the desired product as a white solid. MS (m/e): 381.2 (MH+, 100%)

Example 188

[6-(1-Cyclopropyl-piperidin-4-yloxy)-naphthalen-2-yl]-morpholin-4-yl-methanone

Step 1: 3-[Cyclopropyl-(2-ethoxycarbonyl-ethyl)-amino]-propionic acid ethyl ester:

A mixture of ethyl acrylate (30.0 g, 300 mmol, 2.0 eq.) and cyclopropyl amine (8.5 mL, 149 mmol, 1.0 eq.) in absolute ethanol (45 mL) was stirred 24 h at room temperature. The crude mixture was purified by fractionated distillation in vacuo (20 mbar). One fraction was collected (boiling point: 135° C. at 20 mbar), yielding to 20.58 g (54%) of the desired product as a colorless oil. MS (m/e): 274.3 (MH+, 100%).

Step 2: 1-Cyclopropyl-piperidin-4-one:

A solution of 3-[cyclopropyl-(2-ethoxycarbonyl-ethyl)-amino]-propionic acid ethyl ester (10.0 g, 39 mmol, 1.0 eq.) in anhydrous tetrahydrofuran (65 mL) was added dropwise to a solution of sodium hydride (60% oil dispersion, 2.33 g, 58 mmol, 1.5 eq.) in anhydrous tetrahydrofuran (65 mL). Absolute ethanol (1.79 g, 39 mmol, 1.0 eq.) was then added. The resulting mixture was heated under reflux for 24 h. The solution obtained was neutralized (pH: 7) with diluted acetic acid and partitioned between water and ethyl acetate. The aqueous layer was extracted with ethyl acetate. The combined extracts were dried over sodium sulfate and the solvent was removed in vacuo, yielding to 10.2 g of reddish oil.

This crude oil was then heated under reflux in 18% w/w hydrochloric acid (130 mL) for 5 h. After basification with sodium hydroxide (ca. 31 g, pH: ca. 12), the crude mixture was extracted with ethyl acetate. The combined extracts were dried over sodium sulfate and the solvent was removed in vacuo. The crude mixture was purified by fractionated distillation in vacuo (20 mbar). One fraction was collected (boiling point: 75° C. at 20 mbar), yielding to 3.6 g (67%) of the desired product as a colorless oil. MS (m/e): 140.0 (MH+, 100%).

Step 3: 1-Cyclopropyl-piperidin-4-ol:

To a cold (0° C.) solution of 1-cyclopropyl-piperidin-4-one (1.5 g, 11 mmol, 1.0 eq.) in absolute ethanol was added sodium borohydride (306 mg, 8 mmol, 0.75 eq.). The reaction mixture was stirred at room temperature for 65 h. The mixture was concentrated in vacuo. Ice water (10 mL) was added, followed by an aqueous solution of sodium hydroxide (28% w/w, ca. 10 mL) and dichloromethane (20 mL). The mixture was stirred at room temperature for 2 h. After phase separation, the aqueous layer was extracted with dichloromethane. The combined organic layers were washed with brine, dried over sodium sulfate, filtered and evaporated in vacuo. The crude mixture was purified on silica eluting with DCM/2N NH3 in methanol 93/7, yielding to 1.44 g (95%) of the desired product as a colorless oil. MS (m/e): 423.1 (MH+, 100%)

Step 4: 6-(1-Cyclopropyl-piperidin-4-yloxy)-naphthalene-2-carboxylic acid methyl ester.

Hydrochloric Acid Salt:

To a solution of 1-cyclopropyl-piperidin-4-ol (272 mg, 1.9 mmol, 1.3 eq.) in tetrahydrofuran (7 mL) was added a solution of 6-Hydroxy-naphthalene-2-carboxylic acid methyl ester (commercially available) (300 mg, 1.48 mmol, 1.0 eq.) in tetrahydrofuran (5 mL) and tri-n-butylphosphine (600 mg, 2.96 mmol, 2 eq.). A solution of azodicarbonyl-dipiperidine (749 mg, 2.97 mmol, 2.0 eq.) in tetrahydrofuran (5 mL) was added within 3 min. The reaction mixture was stirred 48 h at room temperature. The reaction mixture was concentrated in vacuo, stirred in 15 mL dichloromethane/heptane 1/1 v/v and filtered. The solid was washed with 15 mL of dichloromethane/heptane then discarded. The liquor was concentrated in vacuo. The crude mixture was dissolved in ethyl acetate (10 mL). A solution of hydrochloric acid in ethyl acetate (2.23 M, 4 mL) was added, followed by methyl-tert-butyl ether (10 mL). The resulting mixture was stirred 2 h at 0° C. then filtered. The solid was washed with methyl-tert-butyl ether then dried in vacuo, yielding to 240 mg (45%) of the desired product as a white solid. MS (m/e): 362.7 (MH+, 100%).

Step 5: [6-(1-Cyclopropyl-piperidin-4-yloxy)-naphthalen-2-yl]-morpholin-4-yl-methanone:

To a solution of 6-(1-cyclopropyl-piperidin-4-yloxy)-naphthalene-2-carboxylic acid methyl ester hydrochloric acid salt (205 mg, 0.57 mmol, 1.0 eq.) in a mixture of tetrahydrofuran (3 mL), methanol (1.5 mL) and water (1 mL) was added lithium hydroxide (52 mg, 1.25 mmol, 2.2 eq.). The mixture was stirred at 45° C. overnight. The crude mixture was concentrated in vacuo. Water (2 mL) was added and the suspension was acidified (pH ca. 2) with hydrochloric acid. The solution was concentrated in vacuo.

This crude mixture was dissolved in dimethylformamide (5 mL). O-Benzotriazol-1-yl-N,N,N',N'-tetramethyluronium tetrafluoroborate, morpholine and diethyliso-propylamine were added. The crude mixture was stirred at room temperature for 24 h. The mixture was partitioned between ethyl acetate and a sodium hydrogenocarbonate aqueous saturated solution. The aqueous layer was extracted with ethyl acetate and the combined organic layers were evaporated in vacuo. The crude mixture was purified on silica eluting with DCM/2N NH3 in methanol 97/3, yielding to 145 mg (67%) of the desired product as a white solid. MS (m/e): 381.5 (MH+, 100%)

Example 189

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |

-continued

| Ingredients | Per tablet | |
|---|---|---|
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example 190

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 191

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 192

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |

-continued

| | |
|---|---|
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to procedures typically used in the art.

Example 193

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with Magnesium stearate and the flavouring additives and filled into sachets.

Example 194

The following test was carried out in order to determine the activity of the compounds of formula (I):

Binding Assay with $^3$H-(R)α-Methylhistamine:

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R)α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4:

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 μl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit Ki values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 1 | 26 |
| Example 13 | 111 |
| Example 31 | 571 |

It is to be understood that the invention is not limited to the particular embodiments of the invention described above, as variations of the particular embodiments may be made and still fall within the scope of the appended claims.

What is claimed is:
1. A compound of the formula I:

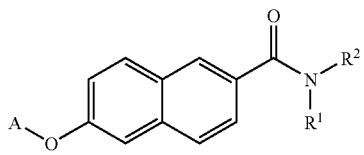

I wherein:
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur,
said saturated heterocyclic ring
being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or
being condensed with a phenyl ring, said phenyl ring being unsubstituted or substituted by one, two or three groups independently selected from lower alkyl, lower alkoxy and halogen;

A is

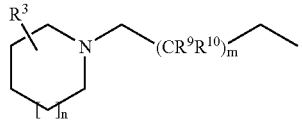

A1 wherein:
m is 0, 1 or 2;
n is 1;
$R^3$ is hydrogen or lower alkyl;
$R^9$ and $R^{10}$ are independently from each other selected from hydrogen or lower alkyl;
and pharmaceutically acceptable salts thereof.

2. The compound according to claim 1, wherein:
$R^1$ and $R^2$ together with the nitrogen atom to which they are attached form a 5- or 6-membered saturated heterocyclic ring optionally containing a further heteroatom selected from nitrogen, oxygen or sulfur, said saturated heterocyclic ring being unsubstituted or substituted by one, two or three groups independently selected from lower alkyl, lower alkoxy and oxo, or being condensed with a phenyl ring, said phenyl ring being unsubstituted or substituted by one, two or three groups independently selected from lower alkyl, lower alkoxy and halogen;
A is

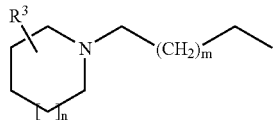

A1' wherein:
m is 0, 1 or 2;
n is 1;
$R^3$ is hydrogen or lower alkyl;
and pharmaceutically acceptable salts thereof.

3. The compound according to claim 1, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen.

4. The compound according to claim 1, wherein $R^1$ and $R^2$ together with the nitrogen atom to which they are attached form a heterocyclic ring selected from the group consisting of piperidine, piperazine, pyrrolidine, thiomorpholine, morpholine and azepane, said heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen.

5. The compound according to claim 1, wherein $R^1$ and $R^2$ together with the nitrogen atom to which they are attached form a 5- or 6-membered saturated heterocyclic ring optionally containing a further heteroatom selected from nitrogen, oxygen or sulfur, said saturated heterocyclic ring being unsubstituted or substituted by one, two or three groups independently selected from lower alkyl, lower alkoxy and oxo, or being condensed with a phenyl ring, said phenyl ring being unsubstituted or substituted by one, two or three groups independently selected from lower alkyl, lower alkoxy and halogen.

6. The compound according to claim 1, wherein A is of the formula A1:

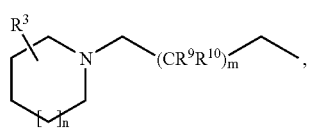

A1 wherein m is 0, 1 or 2; n is 1; $R^3$ is hydrogen or lower alkyl, and $R^9$ and $R^{10}$ are independently from each other selected from hydrogen or lower alkyl.

7. The compound according to claim 6, wherein $R^9$ and $R^{10}$ are hydrogen.

8. The compound according to claim 6, wherein m is 1 and n is 1.

9. The compound according to claim 1, wherein said compound is selected from the group consisting of:

piperidin-1-yl-[6-(3-piperidin-1-yl-propoxy)-naphthalen-2-yl]-methanone, (4-methyl-piperidin-1-yl)-[6-(3-piperidin-1-yl-propoxy)-naphthalen-2-yl]-methanone, (4-isopropyl-piperazin-1-yl)-[6-(3-piperidin-1-yl-propoxy)-naphthalen-2-yl]-methanone, (2-methyl-pyrrolidin-1-yl)-[6-(3-piperidin-1-yl-propoxy)-naphthalen-2-yl]-methanone, (3,4-dihydro-1H-isoquinolin-2-yl)-[6-(3-piperidin-1-yl-propoxy)-naphthalen-2-yl]-methanone, (3,4-dihydro-1H-isoquinolin-2-yl)-{6-[3-(2-methyl-piperidin-1-yl)-propoxy]-naphthalen-2-yl}-methanone,

[6-(3-piperidin-1-yl-propoxy)-naphthalen-2-yl]-thiomorpholin-4-yl-methanone, (4-methoxy-piperidin-1-yl)-[6-(3-piperidin-1-yl-propoxy)-naphthalen-2-yl]-methanone,

[6-(3-piperidin-1-yl-propoxy)-naphthalen-2-yl]-pyrrolidin-1-yl-methanone,

{6-[3-(2-methyl-piperidin-1-yl)-propoxy]-naphthalen-2-yl}-pyrrolidin-1-yl-methanone, azepan-1-yl-[6-(3-piperidin-1-yl-propoxy)-naphthalen-2-yl]-methanone 1:1 hydrochloride, (4-benzyl-piperidin-1-yl)-[6-(3-piperidin-1-yl-propoxy)-naphthalen-2-yl]-methanone 1:1 hydrochloride, and (2-isopropyl-pyrrolidin-1-yl)-[6-(3-piperidin-1-yl-propoxy)-naphthalen-2-yl]-methanone 1:1 hydrochloride, or pharmaceutically acceptable salts thereof.

10. The compound according to claim 1, wherein said compound is selected from the group consisting of:

(4-methyl-piperidin-1-yl)-[6-(3-piperidin-1-yl-propoxy)-naphthalen-2-yl]-methanone, (4-isopropyl-piperazin-1-yl)-[6-(3-piperidin-1-yl-propoxy)-naphthalen-2-yl]-methanone, (3,4-dihydro-1H-isoquinolin-2-yl)-[6-(3-piperidin-1-yl-propoxy)-naphthalen-2-yl]-methanone,

[6-(3-piperidin-1-yl-propoxy)-naphthalen-2-yl]-pyrrolidin-1-yl-methanone, and

{6-[3-(2-methyl-piperidin-1-yl)-propoxy]-naphthalen-2-yl}-pyrrolidin-1-yl-methanone, or pharmaceutically acceptable salts thereof.

11. A process for the manufacture of a compound according to claim 1, comprising the steps of:

a) reacting a compound of the formula II:

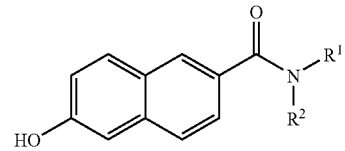

II wherein $R^1$ and $R^2$ are as defined in claim 1,
with an alcohol of the formula III:

HO-A   III wherein A is as defined in claim 1, in the presence of a trialkylphosphine or triphenylphosphine and of a diazo compound to obtain a compound of the formula I:

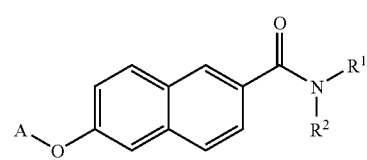

I and if desired, converting the compound obtained into a pharmaceutically acceptable acid addition salt, or, alternatively, b) coupling a compound of formula VII:

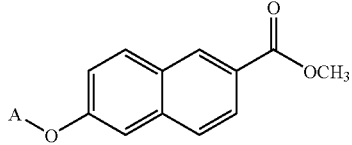

wherein A is as defined in claim 1,
with an amine of the formula V:

wherein $R^1$ and $R^2$ are as defined in claim 1,
under basic conditions to obtain a compound of the formula I:

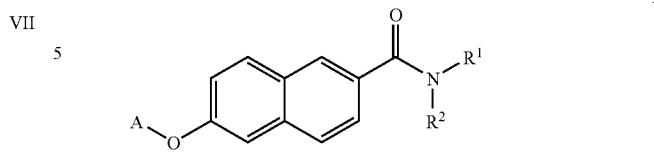

and if desired,
converting the compound obtained into a pharmaceutically acceptable acid addition salt.

12. A pharmaceutical composition comprising a therapeutically effective amount of a compound according to claim 1 as well as a pharmaceutically acceptable carrier and/or adjuvant.

* * * * *